United States Patent [19]
Boyer et al.

[11] Patent Number: 5,157,736
[45] Date of Patent: Oct. 20, 1992

[54] APPARATUS AND METHOD FOR OPTICAL RECOGNITION OF CHEMICAL GRAPHICS

[75] Inventors: Stephen K. Boyer, Springfield, Pa.; Richard G. Casey, Morgan Hill, Calif.; Alex M. Miller, Aptos, Calif.; Bernadette Oudot, Palo Alto, Calif.; Karl S. Zilles, Los Gatos, Calif.

[73] Assignee: International Business Machines Corporation, Armonk, N.Y.

[21] Appl. No.: 688,173

[22] Filed: Apr. 19, 1991

[51] Int. Cl.$^5$ .............................................. G06K 9/00
[52] U.S. Cl. ....................................... 382/10; 382/21; 382/1; 364/496
[58] Field of Search ................. 382/1, 10, 21, 30, 36; 364/496, 497

[56] References Cited

U.S. PATENT DOCUMENTS

| | | | |
|---|---|---|---|
| 4,085,443 | 4/1978 | Dubois et al. | 364/900 |
| 4,205,391 | 5/1980 | Ulyanov et al. | 364/900 |
| 4,473,890 | 9/1984 | Araki | 364/900 |
| 4,530,009 | 7/1985 | Mizokawa | 358/183 |
| 4,555,700 | 11/1985 | Convis et al. | 340/721 |
| 4,633,506 | 12/1986 | Kato | 382/56 |
| 4,677,460 | 6/1987 | Fass et al. | 358/22 |
| 4,686,521 | 8/1987 | Beaven et al. | 340/703 |
| 4,734,769 | 3/1988 | Davis | 358/142 |
| 4,761,818 | 8/1988 | Bannai | 382/41 |
| 4,811,217 | 3/1989 | Tokizane et al. | 364/300 |
| 4,843,569 | 6/1989 | Sawada et al. | 364/518 |
| 4,881,175 | 11/1989 | Ladner | 364/496 |
| 4,949,388 | 8/1990 | Bhaskaran | 382/10 |

FOREIGN PATENT DOCUMENTS 0283267  3/1988  European Pat. Off. .

OTHER PUBLICATIONS

Article entitled "Computational Perception and Recognition of Digitized Molecular Structures" M. Leonor Contreras, et al., J. Chem. Inf. Comput. Sci., vol. 30, No. 3, 1990, pp. 302-307.

Article entitled "Syntactic definition and parsing of molecular formulae" by P. G. Barker, The Computer Journal, (vol. 18, No. 4), 1974, pp. 355-359.

Article entitled "Chemical Symbol String Parser" by J. Figueras from 1983 Chemical Society pp. 48-52.

Primary Examiner—Leo H. Boudreau
Assistant Examiner—Andrew W. Johns
Attorney, Agent, or Firm—Baker, Maxham, Jester & Meador

[57] ABSTRACT

An apparatus and method for optical recognition of chemical graphics allows documents containing chemical structures to be optically scanned so that both the text and the chemical structures are recognized. The structures are converted directly into molecular structure files suitable for direct input into chemical databases, molecular modeling programs, image rendering programs and programs that perform real time manipulation of structures.

22 Claims, 9 Drawing Sheets

FIG. 4

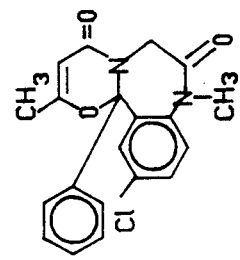

Ketazolam [1971] (kee tay' zoe lam). $C_{20}H_{17}ClN_2O_3$.
368.82. (1) 4H-[1,3]-Oxazino[3,2-d]-[1,4]benzodiazepine-4,7(6H)-dione, 11-chloro-8,12b-dihydro-2,8-dimethyl-(2) 11-Chloro-8,12b-dihydro-2,8-dimethyl-12b-phenyl-4H-[1,3]-oxazino[3,2-d]-[1,4]benzodiazepine-4,7(6H)dione. CAS-27223-35-4. INN
Tranquilizer (minor). Unakalm (Upjohn) U-28,774

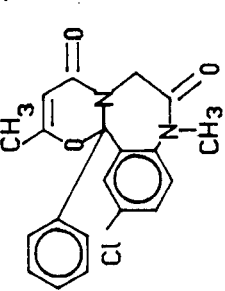

Kethoxal [1969] (kee 'thox' al). $C_6H_{12}O_4$. 148.16. [Ketoxal is INN.]
(1) 2-Butanone, 3-ethoxy-1,1-dihydroxy-)
(2) 3-Ethoxy-1,1-dihydroxy-2-butanone.
CAS-27762-78-3. Antiviral. (Upjohn†) ΦU-2032

Ketazolam [1971] (kee tay' zoe lam). $C_{20}H_{17}ClN_2O_3$.
368.82. (1) 4H-[1,3]-Oxazino[3,2-d]-[1,4]benzodiazepine-4,7(6H)-dione, 11-chloro-8,12b-dihydro-2,8-dimethyl-(2) 11-Chloro-8,12b-dihydro-2,8-dimethyl-12b-phenyl-4H-[1,3]-oxazino[3,2-d]-[1,4]benzodiazepine-4,7(6H)dione. CAS-27223-35-4. INN
Tranquilizer (minor). Unakalm (Upjohn) U-28,774

Kethoxal [1969] (kee 'thox' al). $C_6H_{12}O_4$. 148.16. [Ketoxal is INN.]
(1) 2-Butanone, 3-ethoxy-1,1-dihydroxy-)
(2) 3-Ethoxy-1,1-dihydroxy-2-butanone.
CAS-27762-78-3. Antiviral. (Upjohn†) ΦU-2032

APPARATUS AND METHOD FOR OPTICAL RECOGNITION OF CHEMICAL GRAPHICS

BACKGROUND OF THE INVENTION

This invention relates to the recognition, characterization and representation of chemical notational indicia, including graphic and textual components thereof.

Computers have proven themselves useful as tools for manipulation and display of graphical information, as witnessed by the rapid transition to CAD from manual design systems and the widespread use of desktop publishing. These graphic capabilities are also important in the scientific research environment for modeling and displaying natural phenomena. In the chemical sciences field, graphical requirements are combined with another, the notion of a graphical database that can be searched and accessed on the basis of graphical characteristics.

Today, there are numerous databases comprising vast quantities of chemical and biological information which are dependent on graphic representations of molecules as the critical feature allowing for this data to be accessed graphically via substructure searching techniques. Once a database is created, it serves as the central facility for a wealth of other applications, such as information retrieval, publishing, scientific analysis, etc.

Facilities for entering graphical data are less advanced than those for manipulating it. For many years, this problem impeded the transfer to computers of paper systems, such as, utility maps, engineering diagrams, graphical chemical data, etc. To create a graphical object in digital format, an engineering diagram, for example, requires appreciable time on the part of a trained operator. Frequently, it requires a duplication of effort in the sense that the operator works from an already created printed drawing or hand sketch. Chemical structures that are candidates for addition to databases, for example, are often already printed in journals and catalogs, etc.

SUMMARY OF THE INVENTION

The present invention is directed to an apparatus and method for the automated creation of digital representations of chemical structures from printed matter, including chemical structures represented in graphical form with associated textual components and chemical structures represented solely as character strings. To that end, in accordance with one aspect of the invention, a chemical diagram on a printed page is optically scanned to provide a raw spatial arrangement of black and white elements that is 1:1 with that of the printed page. The scan data is interpreted using a pattern recognition process in order to arrive at a high order description, that of a chemical structure. The pattern recognition process reads printed characters (optical character recognition, OCR), detects lines and determines their interactions, recognizes their geometric shapes, accommodates different drawing conventions, and applies the rules of chemistry to identify the atoms of the chemical structure and the bond connections between atoms. The process further resolves ambiguities and validates results. Character string textual components representing chemical structures or substructures, are drawn in graphical form. If desired, graphical images derived from character string representations and/or scanned directly from the input text may be displayed for evaluation.

BRIEF DESCRIPTION OF THE DRAWINGS

FIG. 4 is another diagrammatic representation of a page of text showing a chemical entry that has been scanned and separated.

DETAILED DESCRIPTION OF THE PREFERRED EMBODIMENTS

There are a number of mathematical equivalent methods of representing the chemical structure of a molecule, e.g., adjacency matrices, connection tables, and link lists. Recent efforts to develop standards for molecular connection tables range from the Brookhaven Protein Data Bank format to the Molecular Design Limited (MDL) MOLFILE format, the Standard Molecular Data (SMD) format and others. See, Barnard, "*Draft Specification for Revised Version of the Standard Molecular Data (SMD) Format*", Journal of Chemical Information and Computer Sciences, 30:81-96, American Chemical Society (1990); Wipke, "*Evolution of Molecular Graphics*", ACS Symposium Series 341 - Graphics for Chemical Structures, American Chemical Society (1987). The output of the optical recognition apparatus and method set forth herein is a molecular structure file that includes a list of nodes (atoms) with their coordinates for a two dimensional representation, plus a connection table defining the bonds between the nodes. The output molecular structure file may be used as an appropriate input format for other applications such as image rendering, text processing, and molecular modeling programs.

A. OVERVIEW

Figures 1, 3:
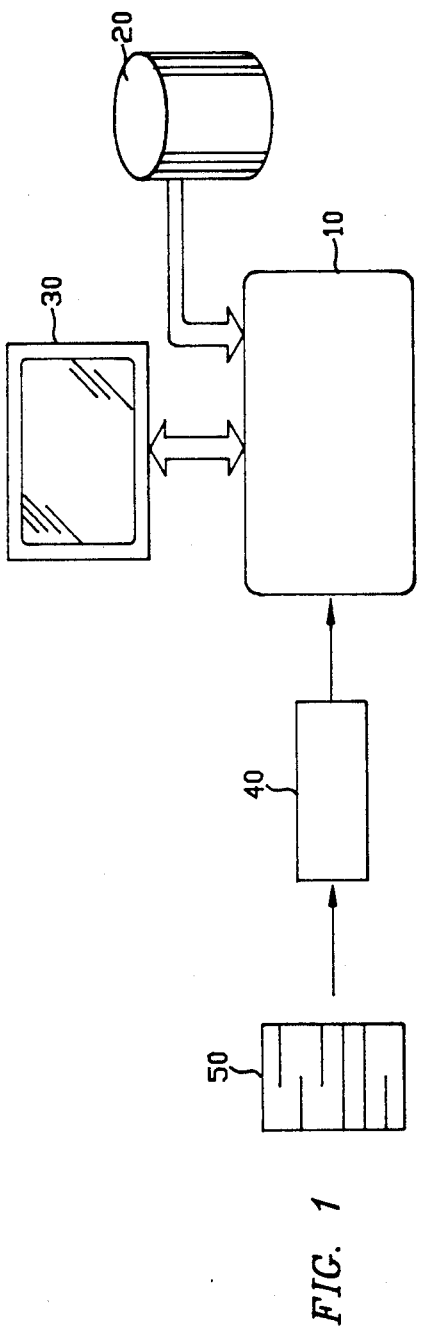
FIG. 1 is a diagrammatic representation of a digital processing apparatus constructed in accordance with the present invention.
FIG. 3 is a diagrammatic representation of a page of text showing a chemical entry that has been scanned and separated.
Figure 2:
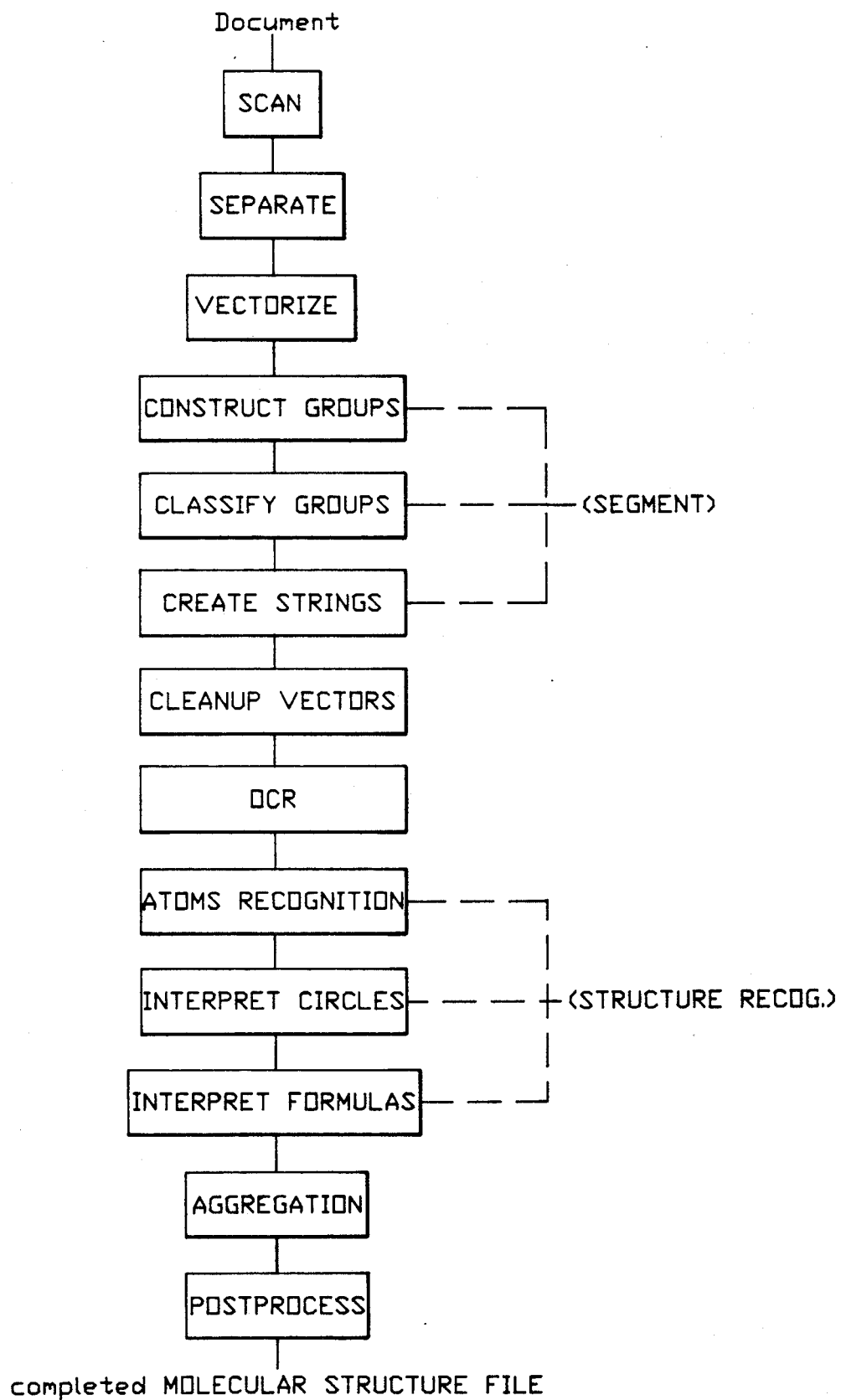
FIG. 2 is a block diagrammatic representation of a functional sequence to be performed by the apparatus of FIG. 1.

Optical recognition of chemical graphics in accordance with the present invention may be performed by the data processing apparatus of FIG. 1, which includes a programmable computer 10 with keyboard, a memory 20, a display monitor 30 and an optical scanning device 40. These components are conventionally known and may include a wide variety of component types and system arrangements. The data processing apparatus is controlled by a software system which may be resident on the memory 20. The software system may also be placed on a variety of data storage media in addition to the memory 20, for example, if the software system is to be transported. Such storage media may include floppy magnetic disks, optical disks, magnetic tape, portable hard disks, and other media. The software system includes an executable instruction set for controlling the data processing apparatus for automatic recognition of chemical structure images formed on an input text 50. The software system controls execution in accordance with the flow diagram shown in FIG. 2. The flow steps include scanning, separation, vectorization, segmentation, cleanup, ocr, structure recognition, aggregation and post processing. These steps are outlined and discussed in detail below.

In one aspect of the optical recognition process, ambiguities in recognizing characters or chemical string types are flagged and displayed on the monitor 30 so that a user may resolve the ambiguity by using a keyboard or mouse input. In this way, a large number of chemical structures and notations can be recognized. In another aspect of the optical recognition process, character strings representing chemical structures or substructures may be drawn in a graphical structural format. If desired, the graphical images derived from character string representations and/or scanned directly from the input text may be displayed on the monitor 30 so that a user may verify the results of the optical recognition process. Further, chemical strings may be input by other means, such as a keyboard, to be drawn and displayed.

B. SCANNING

Optical scanning devices of differing characteristics are available commercially. In the present method, the diagrams and surrounding text are typically printed in black ink on white paper and are of a size convenient for reading. The scanner need only produce a bi-level image at a continuity that preserves visual quality when the image is displayed on a screen or reprinted on paper.

The image, which may be stored in the computer memory 20, consists of a two-dimensional array of 0s and 1s representing white and black, respectively. The 0s and 1s are in one-to-one correspondence with the cells of a grid that can be imagined to overlay the printed page. Because automatic methods for interpretation of text are less discriminating than the human recognition process, the number of cells per unit area has to be greater than, for example, the resolution used in facsimile transmission of documents, which does not exceed 200 cells per inch. Resolutions of 300 samples per inch are suitable, however, and character recognition is not significantly improved at higher resolutions.

C. DETECTION AND SEPARATION OF A DIAGRAM

The Separation step employs an image analysis program that is set forth in detail in pseudocode form in Appendix A, hereto. As shown in Appendix A, and with reference to the sample text inputs shown in FIGS. 3 and 4, the program resolves the scan array into rectangular subimages or "RSIs" each containing a connected component or "cc." The connected components are uniquely defined by two properties. Each connected component is composed of a contiguous set of black pixels, and no two connected components are in contact. The x and y extent of each connected component is computed in the process. These dimensions are the width and height, respectively, of the enclosing bounding rectangle ("RSI") for the connected component.

Next, the system searches for a connected component whose height and width dimensions exceed thresholds w and h, respectively. The parameters w and h are chosen to exceed the maximum character size expected on the page. It is thus assumed that a subimage satisfying the threshold test is a section of a chemical structure.

A search is then made for neighboring connected components within a distance threshold t in the x direction and v in the y direction from the selected connected component. The values t and v are also parameters of the system, chosen to be smaller than the whitespace that separates diagram elements from surrounding text. If any connected components are found within the expanded region provided by t and v, they are combined with the initial connected component to define an enlarged bounding rectangle containing the entire group. The search then iterates using the expanded region. This region growing process terminates when no further connected components are found within the margin determined by t and v.

As an alternative to the above-described process, the separation step could be performed manually by a user using the monitor 30 to display the scanned input text, the user could select the corners of the rectangular subimage using a mouse to position a dragging rectangle over the desired area and clicking a mouse button.

The output of the Separation stage is the subimage for the bounding rectangle determined by the growing process, as well as the list of connected components within this region, as shown in FIGS. 3 and 4. This data is assumed in the subsequent processing to constitute the subimage of the chemical structure and associated characters, as well as the connected component list for the structure and characters, respectively. At this point, the chemical structure and character subimage is referred to as the isolated raster image.

D. VECTORIZATION

Figure 5:
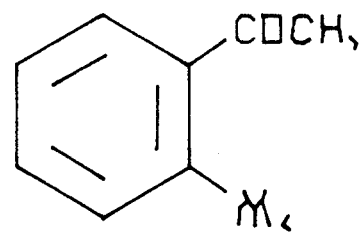
FIG. 5 is a diagrammatic representation of a vectorized image.

A commercially available software package known as the Graphic Image Formatting and Translating System, GIFTS, developed by the assignee of the present application, has been used advantageously for the raster to vector conversion of the structure subimage. An OS/2 adaptation of this program is known commercially as MicroGifts and is part of the IBM CAD Plus Product (Program Number 70F9287). The MicroGifts routines called are MGPREP (preprocess image), MGTAIN (thin lines) and MGRUCIV (vectorize image). Other known vectorization programs could no doubt also be employed in the present process. The vectorization algorithm attempts to fit line segments (i.e., vectors) to the given pixel array, producing as output the endpoint coordinates of the approximating lines. The thickness of each line is also estimated, and end points of lines are labeled as free ends (endpoints), junctions (junctionpoints) (where 3 or more lines meet), loop closures (circlepoints), or connections (chain-points) (2 lines meeting). A typical vector representation of a raster image is shown in FIG. 5.

The vector representation serves as the basis for converting the structure diagrams to a molecular structure file. The vector representation also serves as a basis for determining the positions of characters in the isolated raster image for subsequent OCR processing. The vector description is graphical, consisting of points in space, or nodes, and connections between nodes, i.e., branches. For the vectors representing chemical structure, the vector elements are ideal and depict, respectively, the atoms of a molecule and the bonding between atoms. The vectorization output, however, is an imperfect graph that must be processed further in order to arrive at the molecular structure file corresponding to the selected image.

Two types of imperfections occur in the initial vectorized version of a chemical structure diagram. First, the node information for a molecular structure file is partly symbolic data, e.g., the designation of a chemical element. The vectorization algorithm encodes the entire image as vectors, including printed characters. Furthermore, this representation of characters by vectors is often poor due to noise in printing and scanning, as well as other factors. Consequently, as will be shown below, the vectors derived from characters are used only to distinguish between the characters and other diagram elements. Actual identification of symbols is done by reference back to the isolated raster image from which the vectors were obtained.

Figure 7:
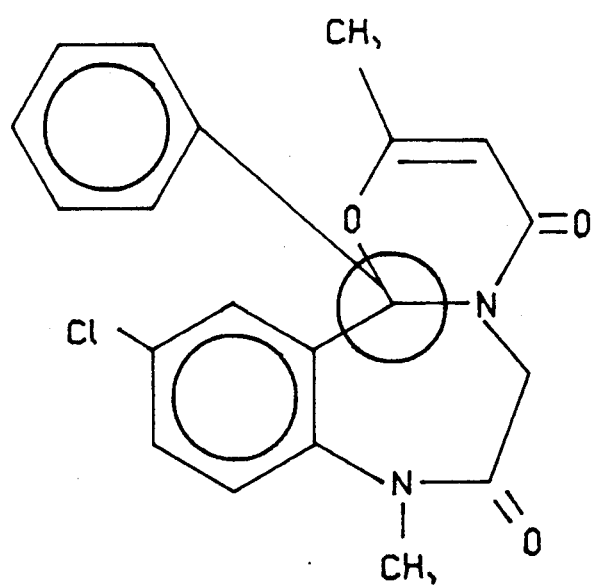
FIG. 7 is a diagrammatic representation of another vectorized image showing an example of imperfect conversion.

Secondly, because the vectorizing algorithm is based on very general principles, a straight line in the diagram may be broken in the approximation, that is, resolved into two or more segments. This happens more frequently in the neighborhood of junctions where several lines connect, but can happen anywhere on the drawing. Thus, the branches, as well as the nodes of the initial graph obtained by vectorization, may be in error, as shown in FIG. 7. It is the task of subsequent stages to consider both the characteristics of the vectorization process and the syntax of structure diagrams in order to achieve an appropriate transformation from one domain to the other.

E. SEGMENTATION OF CHARACTER IMAGES

Vectorization algorithms tend to represent the irregular shapes of most printed characters or text contained within the structure by sets of short vectors. This property can be used to detect characters in the diagram and record their locations. This step is called Segmentation and entails the construction of vector groups and the classification thereof into those derived from character patterns such as text contained within the structure to define various heteroatoms, etc., versus those vectors derived from the rest of the diagram which may be used to define chemical bonds. The Segmentation process also creates strings of connected character vector groups.

It is assumed for purposes of the present discussion that the scanned chemical structure image includes graphical components, such as bonds, benzene rings, etc. and character strings attached to the graphical components. It will be appreciated that many chemical structure representations will contain only character strings. As will be apparent below, the apparatus and method described herein is adapted to evaluate all such formats including input text containing graphical components, character strings or both. The Segmentation process is set forth in detail in pseudocode form in Appendices B, C and D hereto.

As shown and described in Appendix B, the first step of the Segmentation procedure is to assemble the vectors into connected groups. The Construct Group program of Appendix B scans the vectors generated by the vectorization program and arranges the vectors into groups of connected vectors. First, the program creates a set of vertices with associated connectivity information. Each vertex is defined by its x and y position, its status, i.e., endpoint, chainpoint, junctionpoint or circlepoint, and the set of points connected to the vertex. In a second step, the vertices are grouped by the object they describe. The groups are defined by their x and y minimum and maximum positions, class (see below) and the set of vertices in the group.

Following the construction of vector groups, these groups are classified as characters (text within the structure), bond structure, or other symbols, such as circles which are sometimes used by chemists to represent aromatic rings. This is done using the size of each group as follows:

1. Small groups containing only a few vectors are classified by context: if close to another letter they will be classified as a character. This rule accommodates the occurrence of lower case "l", as in the chemical symbol for chlorine, Cl.

2. If the maximum dimension of the group is less than a preset ratio (e.g., 1/6) of the maximum group dimension in the diagram, then the vector is defined as part of a character or text. This ratio is referred to as the text to bond ratio.

3. If the group has at least N vectors (e.g., N=8) and is circular, then the group is classified as a circle. A similar group having fewer vectors is declared a bond.

4. If the group satisfies none of the above, then it is classified as a bond structure.

Referring now to Appendix C, the Classify Groups routine set forth therein assumes that the smallest groups formed by a large number of vertices are characters. Bond groups are deemed to be formed by groups having a large number of vertices and having one dimension that is at least twice as large as the average dimension of the character groups. Dots are deemed to be represented by groups having a height which is less than 0.2 times the average character height. Finally, minus signs are deemed to be formed by small horizontal vectors.

Applying these assumptions, Classify Groups identifies and sorts the groups formed by more than three vertices in accordance with their height and width in ascending order. These groups are searched to find the character groups therein using a text-to-bond ratio test. Beginning with the smallest group, each group with a gheight, (group height) less than two times the median height of all groups previously treated as potential letters (median height initially=gheight of first group) or a gwidth (group width) less than four times the median width of all groups previously treated as potential letters (median width initially gwidth of first group), are classified as letters. The median height and median width are recalculated as each group is treated as the median gheight and gwidth of all groups previously classified as letters. All remaining groups composed of a large number of vertices are classified as bonds or circles. If the number of character groups is equal to the total number of groups, it is assumed that there is no character among the large groups.

All groups composed of less than four vertices are deemed to be bonds if their height or width is greater than 1.8 times gheight or gwidth (i.e., letter size). If the groups are composed of three vertices and are letter size, they are classified as letters. If the groups are composed of two vertices and have a length of less than 0.2 times the height of the smallest group, they are classified as dots. If the group has two vertices and is horizontal and of letter size, the group is classified as a minus sign. Some groups remain unknown until they are classified later by the Create-String process, depending on the context.

Referring now to Appendix D, the Create-String routine for generating character strings is set forth in detail. The Create-String program sorts all groups classified as letters or unknown into horizontal and vertical strings of two or more characters. First, for horizontal strings, all characters are ordered in ascending order depending on their x position. For all characters starting from the left most, a search is made to the left for minus or unknown character size groups. If found, they will be identified as letters and added to the string. A similar search is then made for letter or minus or unknown character size groups on the right. If found, they will be identified as letters and also added to the string. If the search is unsuccessful, the first character does not have neighbors, and no string of length 1 is created during this pass.

To find the vertical string, a similar process is used after ordering all remaining characters on the y scale. This time, all single character strings are also created. If there still are remaining unknown or minus groups, they will be classified a bonds.

Figure 6:
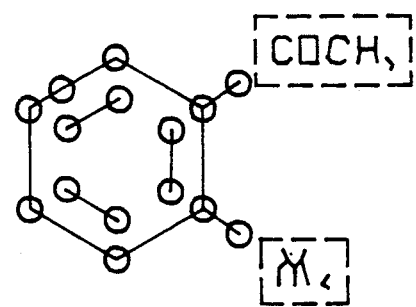
FIG. 6 is a diagrammatic representation of a vectorized image after segmentation.
Figure 8:
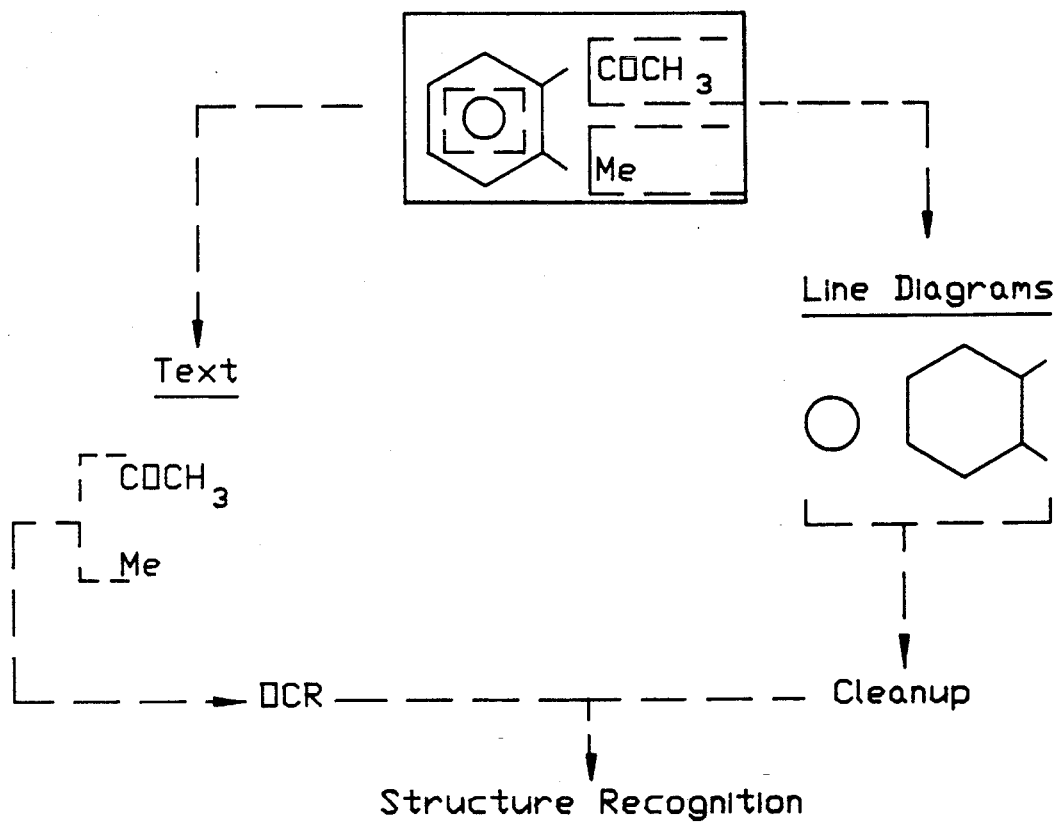
FIG. 8 is a diagrammatic representation showing the segmentation of diagram and residual text.
Figure 9:
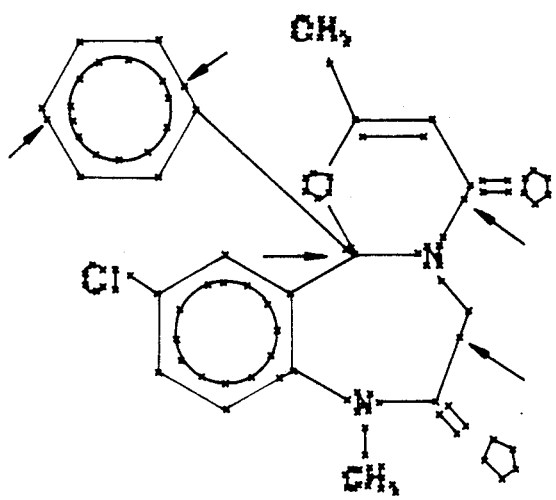
FIG. 9 is a diagrammatic representation of another vectorized image with problem identification.

FIG. 6 shows bounding rectangles that have been drawn around groups which have been classified. FIG. 8 illustrates the overall result of Classify Groups and Create-String as partitioning the vectors into those that specify the bond structure of the diagram and those that make up characters. The bond structure vectors are input to a Vector Cleanup process, described in detail below. The character vectors are processed to determine the bounding rectangles of each group, and the coordinates of these character rectangles are sent to the OCR stage, also described in detail below.

F. VECTOR CLEANUP

Following the classification process described above, the bond structures are processed to remove artifacts incurred during vectorization. The Vector Cleanup process is set forth in detail in pseudocode form in Appendix E hereto. Vector Cleanup is necessary because vectorization algorithms tend to over-vectorize diagrams composed of straight lines. That is, the algorithm may represent a single straight line as several vectors, but seldom does the reverse. The Vector Cleanup stage corrects two types of defects:

1. The breaking of lines in the region of a junction, as seen in the asymmetric central atom in FIG. 10.

2. The breaking of a single diagram line into two or more vectors at points remote from a junction, as seen in the ring structures in FIG. 10.

As shown and described in Appendix E, the first objective is accomplished by detecting any vector with a length less than a specified fraction (e.g., 1/20) of the median value of a line diagram. Such a vector is, in effect, shrunk to a single point, its midpoint. That is, the terminus of any vector connected to the detected one is relocated at the midpoint, and the short vector itself is deleted.

As further set forth in Appendix E, the second case is treated by a procedure that measures the angle of intersection at vertices where exactly two vectors meet. If the angle is less than a predefined value (e.g., 35 degrees), the vertex is removed.

Additional Vector Cleanup steps may be implemented as desired, for example, to remove printing or scanner defects such as broken lines, or for characters that touch the bond structure line. A user interface may also be provided after vectorization to add or delete vectors.

G. OCR

A preferred OCR program which may be employed in the present procedure is disclosed in U.S. Pat. No. 4,499,596. Other OCR programs could no doubt also be employed. The OCR program is modified slightly, which modifications are set forth in detail in pseudocode form in Appendix F hereto.

From the isolated raster image, the OCR process locates and cuts out a character pixel image using the x and y position of the corresponding vector group classified as a character. If a character is wider than a predetermined threshold, indicating that two characters are touching, this process will separate them before normalizing and sending them to the recognition function. Thus, as shown in Appendix E, for separate characters, the OCR program determines a "column of separation" representing the position at which the characters are joined by a minimal number of pixels. The program separates the characters and calls the recognition procedure for each character. The output of the OCR stage is a list of character ID codes in 1-1 correspondence with the bounding rectangles for characters determined prior to the OCR step.

H. STRUCTURE RECOGNITION

If the cleanup routine has operated correctly, the bond structure vectors will accurately represent the connections between atoms portrayed in the printed diagram. The vector connection points are then listed as an array of atoms in accordance with the Structure Recognition process now to be described. This process is shown in detail in pseudocode form in Appendices G, H and I hereto.

The Structure Recognition procedure produces the information necessary to create a molecular structure file, that is, a list of atoms and their graphical coordinates, and a connection table defining the bonds between atoms. To do this, the procedure looks first through the character strings and adds each character to a list of atoms AL. As shown in Appendix G hereto, the Atoms Recognition routine designates the group letters in the character strings as atoms. Each atom is identified by an associated position and a character meaning. The program then searches through each group classified as a bond. For all vertices in the bond groups, the program correlates each vertex representing a junctionpoint (i.e., two or more connections) with a carbon atom C. Otherwise, the program finds the closest atom in the atom list and reports the vertex bond connections to the identified closest atom. Otherwise, if there is no closest atom A, the program adds a new carbon atom C for the vertice.

Aromatic rings may be represented in a diagram by one of several conventions. Often, the bonds are explicitly shown as single or double vectors, and this case is accommodated by the routines described above. A different convention employs a circle in the center of the ring rather than distinct bond lines. The Segmentation process has already checked for the existence of a circle, thus, if one has been found, a special procedure is invoked. This routine, called Interpret Circles, is shown in detail in Appendix H.

The Interpret Circles procedure first arranges all groups classified as a circle by their x position. For each circle group G, there is located a ring of vertices R in the atom list AL that surrounds the circle G. Each ring R is added to a ring list RL. Because molecules sometimes include one or more adjacent sets of three benzene rings sharing common vertices and bonds, the Interpret Circles procedure must accommodate such configurations. To do this, Interpret Circles first searches for all vertices Wi in common within three rings and adds them to a set of such vertices TW. In a loop called START, the Interpret Circles procedure finds paths going through the triple ring vertice in TW that are not fully connected (based on an assumed carbon valence of 4). Starting from the first triple ring vertices in a path, the START loop designates alternating single and double bonds, starting with a single bond, between the successive vertices in the path. Each path is treated accordingly. Thereafter, if all vertices in TW have four bonds, the program jumps to a SINGLE-DOUBLE-RING loop. If each vertex W1 in TW is not fully connected, the procedure adds a double bond from that vertex to a W2 atom common to only two rings and adjacent W1. W2 will be a vertex on the contour of the group of rings. All W2 are added in a set called DW.

In CONTOUR, the process starts from each vertex in DW and navigates around the outer bonds of the rings and designates alternating single and double bonds, starting with a single bond, to the adjacent vertices W2 not in DW and not fully connected. Each treated ring is marked as used. When the process reaches a vertex that is in DW, the CONTOUR loop ends without drawing the last bond, and a new vertex from DW is considered. The SINGLE-DOUBLE-RING section finds all rings not yet marked, including single rings, adjacent rings having only vertices common to two rings at most, or other rings where all vertices to three rings are fully connected. The process finds a vertex W1 of the contour that is a member of only one ring. In the SINGLE-COUNTOUR loop, the procedure navigates around the outer bonds of the rings and designates them as alternating single and double bonds starting with a double bond. The rings are marked as used. When the process reaches the first vertex used, the SINGLE-CONTOUR loop ends without drawing the last bond, and a next unmarked ring is considered.

The next step of the Structure Recognition process is Interpret Formula. As shown in Appendix I, Interpret Formula routine provides character string inputs to the Formula String Processing procedure (Appendix J) and positionally integrates the String Processing output with the graphics structure previously defined (i.e., the list of atoms generated by the Atoms Recognition routine and their positions in a graphics space). If a string is not "useful," i.e., has no connection to the structure, the Interpret Formula routine attempts to find a connection with another string located above or underneath it (see example below):

---
CH3
O
(Bond from structure)

---

A string with no connection is ignored and deleted. The input string to the Formula String Processing program is built with '=' signs representing outliaison connection(s) to the graphics structure. The String Processor produces a list of all atoms involved in the string with their coordinates (in a table space) and a connection table. It also adds one or more fictitious outliaison atoms to the string for outliaison bonds to the graphics structure. The fictitious outliaison atoms correspond to the actual atoms in the structure that are connected to the string, and are used only to insure that the string can be correctly oriented with the graphics structure. A last step of the Interpret Formula routine introduces the table space position information received from the String Processor to the graphics space devised to define the position of the members of the atom list. The table space coordinates are translated into the graphics space using the coordinates of the fictitious outliaison atom(s) as their origin. The Interpret Formula routine adjusts the string position and orientation in the graphics space in the event there is an interference between the string and other structure. If there are two outliaisons, a scaling factor is applied in addition to determining correct string position and orientation.

Interpret Formula defines a rectangle circumscribing the atoms of the string following their translation from the table space to the graphics space. If there is no graphics structure inside the rectangle, or bonds intersecting the edges thereof, Interpret Formula ends. If there is an overlap, Interpret Formula performs symmetry about the x axis and then, if necessary, about the y axis, and again, if necessary, about the x axis, where the x and y axes are defined by the x and y coordinate values (in the graphics space) of the outliaison atom. If an interference still exists, the string is rotated 90 degrees about the z axis extending through the outliaison atom. If an interference continues to exist, x axis - y axis - x axis symmetry is again performed. Thereafter, a 45 degree z axis rotation is attempted, followed by x axis - y axis - x axis symmetry, if necessary. If an interference continues, the Interpret Formula routine calls a FindNext routine that is part of the Formula String Processing procedure. The FindNext routine selects a new bond orientation between the fictitious outliaison atom and the string atom to which it is connected. Interpret Formula terminates when there are no remaining interferences.

In cases where there are two outliaisons, Interpret Formula determines the ratio of the distance between the two outliaison atoms as measured in the graphics space (gd), and the same distance as measured in the table space (td). If gd/td<0, the symmetry is performed about the median extending between the two outliaison atoms in the table space. If gd/td<0.07 or gd/td>1.4, one or both of the string fictitious outliaison atoms are not in their correct positions relative to the remainder of the string. The FindNext routine of Appendix J is called to reorient the first outliaison atom TOut1 and, if necessary the second outliaison atom TOut2, by selecting a new bond orientation between the outliaison atom and the string atom to which it is bonded.

Following the FindNext procedure, or if gd/td is >1.4, a scaling factor of gd/td is applied to the string coordinates. The string is rotated so that the angle between horizontal and a line extending through the two outliaison atoms is equal. Thereafter, the string is translated so that the graphics space and table space positions of the first outliaison atom are coincident. If there is no graphics structure within the rectangle circumscribing the string, and there are no bonds intersecting the edge of the rectangle, Interpret Formula ends. If an interference exists, the procedure incrementally translates the string along a line perpendicular to the line extending between the two outliaison atoms. Each translation increment in the positive and negative direction is one half the value used to define one bond length. If the string is translated eight times at each position of the outliaison atom, two symmetric configurations are tested. User interfacing is employed to resolve any remaining interference.

Appendix J sets forth a detailed description of a Formula String Processing program for processing the character strings input by the Interpret Formula routine. The Formula String Processing program analyzes character strings representing atoms or molecules and represents them by an appropriate atom list and connection table.

The String Processing program is utilized for those portions of the molecule which are more conveniently defined as symbol strings rather than graphical structures. The program applies the rules and conventions used by chemists to represent chemical structures in string form. Utilizing these rules of chemistry, the String Processing program can deal with the most complex strings in organic chemistry and is able to determine the connection table of almost all atom strings found in the literature. Where ambiguities or other errors are detected the errors are flagged and displayed on the monitor so that a user may resolve the ambiguity using the keyboard or mouse input. This may occur, for example, in the case of repeated branched parentheses.

It will be appreciated that a variety of approaches could be employed to obtain a structural representation of a chemical string using the rules of chemistry. For example, a rule-based programming language would be well suited to such a task. Other approaches will no doubt also be apparent in light of the teachings herein and it is contemplated that such approaches may be employed without departing from the scope and spirit of the present invention.

In a preferred embodiment of the present invention, the String Processing program parses the unknown string using a series of routines which isolate molecular group or "front" information from the atoms of the string and which divide the remaining string components into one or more defined substrings for separate processing of each substring into individual connectivity tables. State machines are utilized to perform various actions depending on the character read from the string and the previous state of the state machine. Using one state machine, the program places the front information on a dedicated stack for subsequent use in determining the connectivity between substring groups.

The program also utilizes a general state machine that evaluates and places on a general stack the substring atoms, their valence, information about substring group structure including single and double bond connectivity between elements of the group, the number of inliaison bonds between substrings or substrings, the number of outliaison bonds between the substring and the structure to which the string is attached, the probability that another valence applies for the atom, and pointers to other previously created substring connectivity tables, if any. The general stack data is used together with the substring group information to connect the chemical substring elements in a connectivity table. The substring or elementary substring connectivity table is joined with other substring or elementary substring connectivity tables, if any, until the entire chemical string is represented by a complete table. As each substring or elementary substring is processed the program tests the generated substring connectivity table to insure that all the atoms are fully connected and that all the atoms are in the same molecule. If the testing procedure shows an error, a series of recovery processes commence. The recovery processes are used to change the bond connections between atoms, change the position or number of inliaison bonds (e.g., in the case of repeating parentheses), add triangular bonds, find the atoms that receive an ending valence of a string and modify valences for atoms which may have more than one usual valence. Following testing, a drawing procedure is used to evaluate the substring or elementary substring and determine the coordinate positions of the atoms thereof in a table space coordinate system. Optionally, the drawing procedure can be used to draw string components on the monitor 30 for user evaluation.

As shown in Appendix J, the String Processing routine recognizes certain characters and character structures conventionally used to describe chemical strings. The program recognizes upper and lower case letters, digits, '+' and '−' signs, parentheses '−' separators and commas. It also utilizes the characters '.' and '=' during processing to indicate inliaison and outliaison bond connections between elementary substrings or substrings of the chemical string undergoing processing and between an atom of the chemical string and the structure, respectively.

The program recognizes five general types of chemical strings. They are S0, S1, S2, S4, S5 and S6. The string type S0 is designated as an "elementary substring" that does not include parentheses. The string type S1 is designated as a "substring" that may include parentheses. String types S2–S6 are formed by various combinations of S1 substrings and molecular "front" information. String type S3 (see Appendix J) is not a separate string type. It represents an intermediate step used to generate other string types. As indicated, to simplify the chemical string recognition process, the program divides the input chemical string into substrings and elementary substrings and processes them separately, generating a connectivity table and atom position coordinates for each. As processing proceeds, the connectivity tables are combined to form a composite connectivity table representing the entire string and a list of atoms with their coordinates.

In determining the structural connectivity between the atoms of the chemical substrings, the program tests for the number of repeating carbons therein. Depending on that number, as well as other information (see Appendix J), the program assigns the molecule to one of five (more can be added) chemical structure group types. The group identifications are used to assign certain bond connections between the atoms.

The first recognized group type is the linear group. Chemical strings having more than two but not six repeating carbons are considered linear groups. Such groups may have additional elements or molecules of valence 1 attached thereto as well as one or more "S1" substrings. Another form of linear group may contain six repeating carbons but more than six adjacent hydrogens or other repeating atoms. Finally, another form of linear group may contain two repeating carbons and more than four adjacent hydrogens and another repeating atom of valence 1. The second recognized group type is the cycle group or benzene ring. Cycle groups have exactly six repeating carbons and not more than six adjacent hydrogens or repeating atoms of valence 1, and may have one or more "S1" substrings. The third recognized group is the double linear or ethyl group. Substrings in this group include exactly two repeating carbons together with "front" or group information, or include exactly two repeating carbons and no more than four adjacent hydrogens or another repeating atom of valence 1. The fourth recognized group is the Sulfur group. Substrings in this group include a sulphur atom of valence 2, or a sulphur atom of valence 4 and one oxygen atom connected to the sulphur by a double bond, or a sulphur atom of valence 6 and a maximum of 2 oxygen atoms connected to the sulphur by a double bond, and up to 2 additional oxygen atoms connected to the sulphur by a single bond. The fifth recognized group is the Nitrogen group. Substrings in this group include a nitrogen atom of valence 3 and one oxygen connected to the nitrogen by a double bond, or a nitrogen atom of valence 3 and two oxygens in a form $S1(N+)(O-)-0$, where there is allowed a double bond between the nitrogen and one oxygen, or a single bond between the nitrogen and the second oxygen and a single bond between the nitrogen and S1. It is anticipated that additional groups could be added as desired.

Front information consists of alpha-numeric characters in the string used to impart information about molecular structure. The chemical string recognition program assumes the well known symbols i, iso, n, s, sec, t, tert, cis, trans, p, para, m, meta, o, ortho, and various digits associated therewith, represent front information. The program ignores the notations 1 and d because this information pertains to three dimensional molecular representations. The program also ignores the characters L, D, R, S, CIS and TRANS. These characters can be used to represent existing atoms and may create an ambiguity between atomic symbols and front information.

The output of the String Processing program is an atom list and a connectivity table. The atom list is a list of the atoms of the string and their coordinates (except hydrogen) together with outliaison information indicating how the structure is bonded to other molecular components. The connectivity table is a two dimensional array referring twice to each of the listed atoms. The elements of the array are integers that represent the valence bond between two atoms of the molecule. An example of the output for the molecule CH2CHOH would be as follows:

| Atom List | C(1) | C(2) | O(3) |
|---|---|---|---|
| Outliaison | 0 | 0 | 0 |
| Connectivity table | | | |
| | C(1) | C(2) | O(3) |
| C(1) | X | 2 | 0 |
| C(2) | X | X | 1 |
| O(3) | X | X | X |

Figure 12:
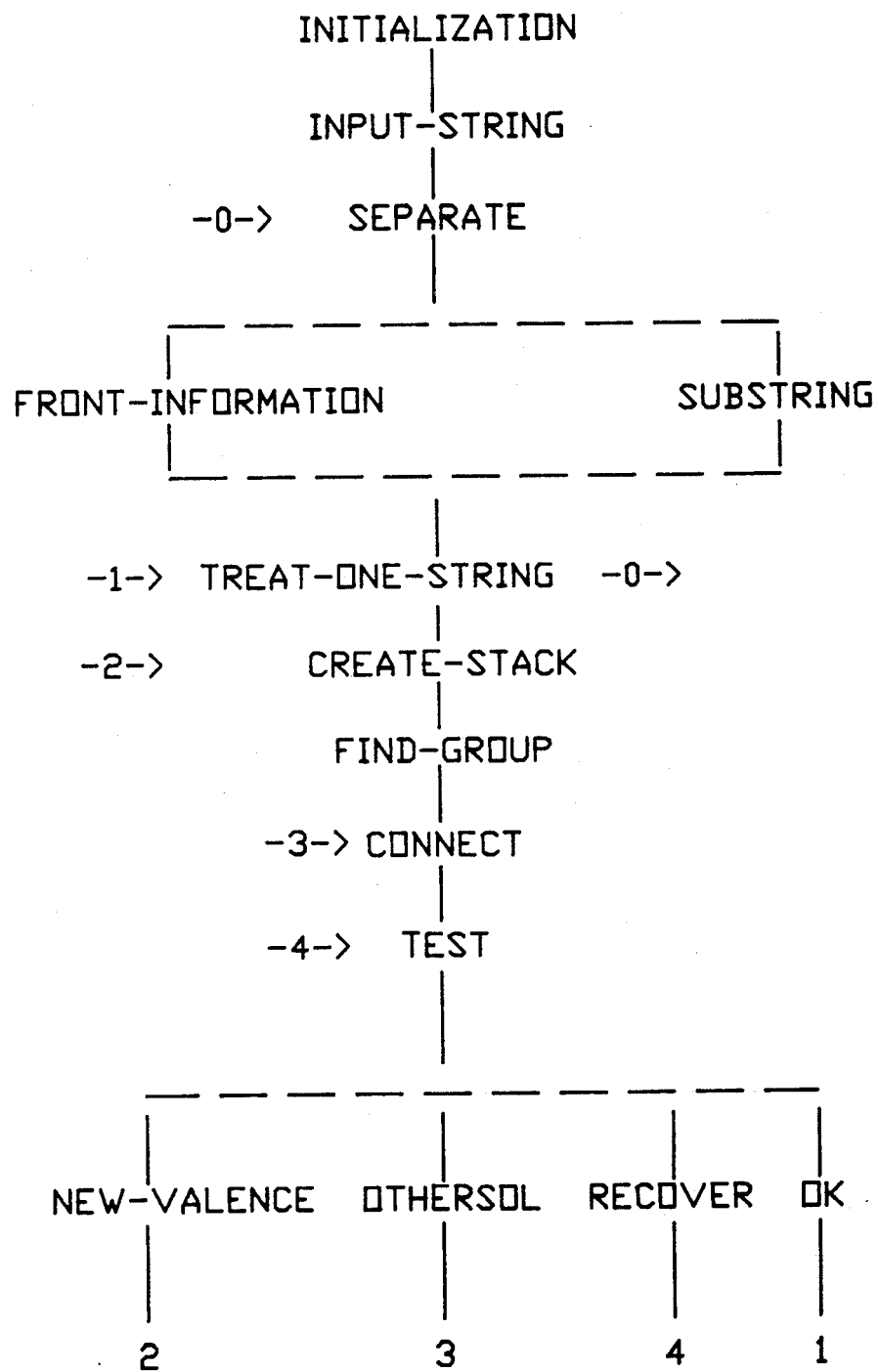
FIG. 12 is a block diagrammatic representation of a chemical string recognition sequence to be performed by the apparatus of FIG. 1.

A flow diagram of the String Processing program is shown is FIG. 12. The program Initializes by reading a user generated valence table from a file which contains a list of atoms and their usual valences. If an atom has more than one possible valence, a valence probability may be assigned. Predefined compounds may also be considered, such as Me for CH3 or Ph for C6H5. These compounds may be declared in the valence table. A preferred compound may be detected directly with a formula string, or indirectly with the name of a molecular structure file. Their names must start with an upper case letter followed by a lower case character. If an atom name is not found in the valence table, the program returns to the character recognition step and attempts correction depending on the context.

Figure 13:
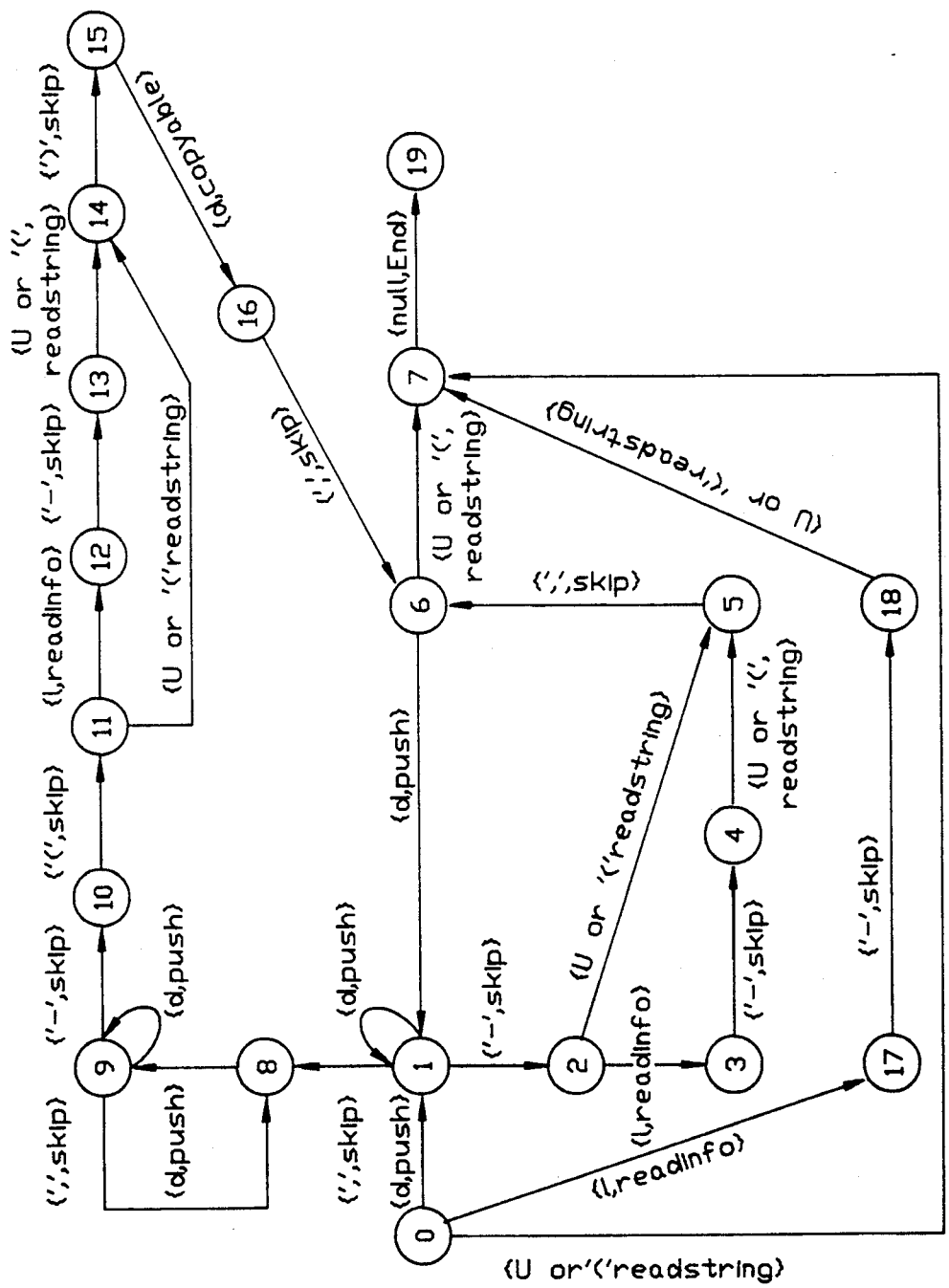
FIG. 13 is a diagrammatic representation of a state machine used to separate chemical front information from substring atom representations.

The program proceeds to the Input-String procedure wherein the string is input together with any outliaison information indicating connection to the graphics portion of the molecule. The string is input to the Separate routine whose function is to separate front (i.e., "group") information from the substring components representing atoms. As a rule of chemistry, only strings having more than one substring (of type S1 or S2) will include digital front information. The Separate routine utilizes a state machine to generate a stack identified as GSTACK and separate the different substrings of type S1. The state machine has 20 different states, 0-19. The Separate routine initializes the state machine to the zero state and creates an empty GSTACK. The program then successively reads the characters in a substring to be treated and performs certain actions depending on the character type and the current state of the state machine. As shown in FIG. 13, the state machine also changes state after the action is taken depending on the type of the new character read from the string. The actions taken by the separate program are as follows:

1. Push—Push digital front information to the GSTACK.

2. Readinfo—Read the front information, and if the front information is not ignored, push the front information to the GSTACK.

3. Readstring—Read a substring, and loop through the Treat-One-String, Create-Stack, Find-Group, Connect and Test routines, wherein the substring is the initial input and a connectivity table for that substring is the final output.

4. Copytable—Create a new connectivity table identical to the connectivity table created during the readstring sequence. The copytable action is used for long strings of the type S6 wherein a substring occurs twice in the molecule.

The process of separating front information from the immediately following substring, and thereafter treating the substring to form a substring connectivity table, repeats until the end of the input string is reached. In the case of multiple substrings with digital front information, the digits report the position of previous substrings relative to the last substring of the string. The program is thus able to modify connectivity tables previously created.

As indicated, after separating the front information from a substring, the Separate routine calls the Treat-One-String routine, which in turn calls the Create-Stack and Connect routines, and the Draw Molecule Procedure, in order to generate an atom list with coordinate positions, and a connectivity table for the substring. The Treat-One-String routine, however, attempts to further divide the substring into elementary substrings (of type S0). If elementary substrings are found within the substring, they are treated separately and their connectivity tables are successively combined. Treated elementary substrings are replaced by a '.' in the substring in which they were located. The presence of '.' means that there exists one or more elementary substrings already treated with a combined connectivity table pointed to by a pointer WT. As each elementary substring and substring is encountered during the Treat-One-String routine, successive calls are made to the Create-Stack and Connect routines and the Draw Molecule procedure.

The Create-Stack routine parses the input elementary substring one character at a time. The output is a stack with all atoms composing the molecule (except hydrogen) and various information related thereto. As discussed above, this information is the atom's valence, structural information about the substring, the number of in- and outliaison bonds, the probability that the atom has another valence, and a pointer to a connectivity table to insert (in case there is a "." in the elementary substring). This information is used to assemble the connectivity table, Test the table and Recover in case of error. If the character read by Create-Stack is a defined compound symbol, such as Me for methane, atoms of the compound are placed on the stack with parentheses.

The Create-Stack routine uses a state machine having 9 different states, 0-8, to perform a variety of stack manipulations and other actions depending on the character read from the string and the existing state of the state machine. As shown, in FIG. 14, the state machine also changes state when an action is taken. The actions taken by the Create-Stack routine as it reads each string character are as follows:

1. Push—Push the character and its most likely valence on the stack.
2. Combinlia—Add inliaison information with a previously treated elementary substring by executing an addpush action and then pushing the atom(s) from the connectivity table of a previously treated elementary substring having an inliaison value that is not null. The valence of each atom pushed to the stack during the combinlia action is the value of the inliaison for the atom and not its valence.
3. Comblia—Add outliaison information with another substring.
4. Addpush—Combine the valence of the character with the valence of the last element on the stack to generate a new resultant valence for that element.
5. Pushlow—Combine the character (a lower case letter) with the last element of the stack to generate a new element having a new valence.
6. Adddnewval—Combine the character (a digit) with the valence of the last element of the stack.
7. Suppush—Delete ( ) from the stack and push the character to the stack.
8. Repeat—pull the last element of the stack (a digit d), duplicate the previous element (d − 1) times and push the present character to the stack.
9. Suprep—Pull the last element of the stack (a digit d), delete () from the stack, duplicate the characters that were between the () d−1 times and push the present character to the stack.
10. Mult—In case of a digit, combine the tens and units digit to create a correct numeric value.

Following the Create-Stack routine, the program initiates the Connect routine. The Connect routine, in turn, makes calls to the Find Group and Test routines, and if necessary, to various Recovery routines. Before calling Find group, Connect adds an inliaison bond to the first atom of an elementary substring that is partial having a valence greater than one. If the substring is not partial, Find group is called without the introduction of inliaison information.

The stack generated by Create-Stack and the applicable front information identified during the Separate routine are input to the Find Group routine. The output will be a modified stack which may have its atoms rearranged, additional atoms inserted from other tables (in case digital front information is present), and new valences reflecting the connections between the atoms, or the attachment of Hydrogen, and structural information modified in accordance with the front information and the type of group recognized. If the substring is determined not to contain a group, no action will be taken.

As previously discussed, the String Processing program utilizes conventional rules of chemistry to recognize linear groups, ring groups, double linear groups, nitrogen and sulfur groups. If a linear group is found, the Find Group routine alters the carbon valences to reflect the assignment of hydrogen atoms to the carbons to fill up each carbon in sequential order. It also determines which non-carbon atoms should be arranged on the stack before the first carbon and after the last carbon. The routine interleaves the remaining atoms between the carbons. If a ring group is found, the Find Group routine alters the carbon valences to reflect the assignment of the Hydrogens and modifies the structural information to assign single and double bonds between the carbons. It also determines the number of atoms occurring before the first carbon and after the last carbon, or between two carbons, depending on the number of hydrogens and other atoms in the group. If a double linear group is found, the routine alters the carbon valences to reflect the assignment of the Hydrogens, and modifies the structural information to assign the double bonds between the carbons. Ambiguities encountered during group formation are flagged out. Similar valence and structural information changes to reflect bond placement determinations are performed by the nitrogen group and sulfur group routines, as shown in the pseudocode listing of Appendix J.

From the modified stack output of Find Group, the Connect routine creates a connectivity table using a Connect Bond routine. The Connect Bond routine loops through the stack three times. During the first pass, the routine connects all atoms of valence 1 to the preceding atom if its valence is greater. During the second pass, the routine connects the group atoms in accordance with the connections determined during the Find-Group routine. During the third pass, all remaining atoms are connected so that all of the atoms are connected.

The Connect routine then calls a Test routine wherein the connectivity table is tested to determine that all atoms are fully connected and that the atoms of the substring are all in a single molecule. If an error is discovered, one or more of the Recover, New valence and Othersol Recovery routines are called by Connect. Otherwise, the program implements the Draw Molecule procedure.

The Recovery routines cut and add different bonds depending on the location of the atom in the string, or add or move inliaison bonds. In some cases, a Recovery routine adds triangular bonds. In other cases, an ambiguity in string nomenclature may be reported. In still other cases involving atoms having more than one usual valence, the valence may be modified and the Connect process repeated.

In the New Valence routine, the valences of partially connected atoms, or their neighbors, having more than one possible valence, are modified and the program returns to Find Group with the modified stack as input. A first Process 1 is used when an atom i is not fully connected. The process tries to find a smaller valence for i, or an atom j before i with a new valence higher than used in the first treatment. A second Process 2 is used when the string has been arbitrarily cut such that there is more than one apparent molecule and the Recover process has been used on one of the apparent molecules. The process finds a new higher valence for an atom j before i. Following Process 1 and Process 2, Find Group is recalled.

In the Othersol routine, connectivity errors are corrected in strings ending with "t" or "−" sign by adjusting the connectivity of atoms that can support the sign. The procedure is used when a molecule has an ending sign and no solution is found when the sign is reported to the last atom of the string. The process goes through the string to find the atom that can support the sign. If there is more than one solution, the ambiguity is reported to the user. The result of Othersol is a modified stack that is input to Connect Bond in order to generate a modified connectivity table.

In the Recover routine, four processes are used for ensuring full atom connection. Recover generates a modified connectivity table for input to the Test Procedure. A first Process 1 of the Recover routine, is used when there is an elementary substring between parentheses followed by a digit, and the last atom of valence >1 is not fully connected, a value of 1 is left over, and the molecule is not cut. Process 1 modifies the connectivity table by adding an inliaison value of 1 to the last atom not fully connected. A second Process 2 of the Recover routine is used when there is an elementary substring between parentheses at the beginning of the string having a last atom of valence >1 not fully connected, a value of 2 is left over, and the molecule is not cut. The process modifies the connectivity table by adding an inliaison value of 1 to the last atom, deleting the inliaison from the first atom, and adding a bond connection between the first and last atoms. A third Process 3 of the Recover routine, is used when one atom is not fully connected, an even number of valences are left over, and the molecule is cut just before i. The process modifies the connectivity table by cutting the bond between the two previous atoms and connecting each previous atom to the not fully connected atom. It may form a triangular bond. A fourth Process 4 of the Recover routine is used when there is more than one apparent molecule that is not fully connected. In the second molecule the process finds the first carbon (firstC) and the last atom (lastA) in the string connected to it. The process then finds a carbon (lastC) between the FirstC and LastA that is connected to firstC. The process modifies the connectivity table by disconnecting FirstC and LastA, FirstC and LastC, and connecting LastC and LastA. If FirstC is not fully connected Process 3 of Recover is used to provide the connection.

Following the Connect routine, the Draw Molecule procedure commences. The purpose of this procedure is to define the coordinate positions of all atoms of the connectivity table generated during the connect routine. With the connectivity table(s) generated by Connect as input, the Draw Molecule procedure determines the coordinate positions of the atoms in each substring or elementary substring treated by Treat-One-String and creates an atom list including coordinate positions. The substring atom lists are combined until an atom list representation of the entire chemical string substructure is created. The final atom list output is returned to Interpret Formula for positioning from a table space to a graphics space for orientation with existing graphical structure, if any. The molecule drawing program utilizes three procedures: Draw Molecule, Find Structures, and FindNext Position. Draw Molecule makes calls to Find Structure in order to determine information regarding the structural characteristics of the input string. Draw Molecule prioritizes the string components using these structural characteristics. As each string structure is processed, a selected routine in Draw Molecule is activated. The selected Draw Molecule routine makes calls to FindNext Position, which determines the positions of the string atoms undergoing processing. Given the position of a first atom a, the FindNext Position procedures determine the positions of atoms b extending from a. Each atom is assigned 8 possible directions to its neighbors. These directions are 45 degrees apart and are represented by integers (0 to 7). If an initially selected next atom direction is unavailable, one or more additional directions are tested until an open direction is found. A mask is associated with each atom to memorize the directions filled with bonds. The position of an atom b determined to lie at a selected direction from an atom a is found by performing a translation following the selected direction from the position of atom a. An atom position is in the form (x, y, b1) (normalized representation) where b1 is the bond length unit because all translations will be given in b1 multiples. This representation allows rotation, translation and symmetry to be performed using matrix operations. Thus, the drawing procedure utilizes a grid having x and y gradations of one b1 each. In case of error, a backtracking mechanism is used until the critical point is reached. At that point, a new direction is used to position the next atom, and the structure is rebuilt.

When Draw Molecule is called in Treat-One-String, it first creates an atom list called ALLATOM in which the atoms of the treated substring are classified in decreasing order by the number of other atoms to which they are connected. Each atom is initialized with a MASK value of 0, indicating that all bond directions are open. If an atom in the table contains a pointer to another table, indicating an inliaison connection, the table pointed to is checked. If the inliaison atom a in the table pointed to was assigned BZ or ET structure information, that information is transferred from the table pointed to and assigned to the stack variable Str(m) in the table being treated.

Draw Molecule then calls a Find Clist routine in the Find Structures procedure. Clists are linear lists of repeating carbons joined by single bonds and not part of an ethyl group. The Clist routine is a conventional deep first search algorithm of the type commonly used to find all of the paths in a tree having multiple roots and bidirectional branches. In this case, the tree is adapted to the connectivity table generated by Connect. The only loops possible are formed by triangular bonds or benzene rings which are marked as a node having no further paths. The Clist routine starts from a first carbon atom as a root node and finds a path of connected carbon atoms extending to a leaf node or to a triangular bond or benzene structure. These atoms are represented as a list of atoms Path{i}, indexed by i. This list is copied as a List{n} and the path is retraced from the leaf node to the next previous node. The program tests for branches from that node. If branches are found they are followed to a leaf node and copied in List{n}. If there are no branches from the previous node, the node is marked. Clist continues until all possible paths have been tested and lists List{n} generated.

Unusable lists, such as duplications in inverse order, etc. are deleted, and Clists ending with benzene rings are inverted, by Draw Molecule. Draw Molecule assigns a linear list (LL) structure designation to all atoms that are not assigned a benzene (BZ) designation. Draw Molecule then calls Find Triangular Bond in the Find Structures procedure. This routine assigns a triangular bond (TB) structure designation to all atoms that are part of a triangular bond.

Draw Molecule selects a first Clist to treat. The selection process is performed in a prioritized manner wherein carbon lists starting and ending with a benzene ring are selected first, beginning with the longest such list. Carbon lists starting with a benzene ring are selected next, beginning with the longest such list. Carbon lists without attached benzene rings, but having the greatest length, are selected as the final priority, beginning with the longest list. Assuming there is a list starting and ending with a benzene ring, or a list starting with a benzene ring, the Draw Molecule procedure assigns the first atom fa a position POS(fa) (0, 0, b1). It also sets the variable PROCESSLIST{i} to fa. PROCESSLIST is a list of atoms that have been drawn and is used for backtracking in the event of a positioning error. Draw Molecule then calls a DrawRing routine, which is part of the Find Next procedure (set forth in detail in Appendix J). The DrawRing routine determines the position of the benzene ring atoms after fa. Initially, however, if fa is an atom having an inliaison connection to another table previously created and drawn, DrawRing searches for a table to insert at the position of the first atom fa. If such a table is found, DrawRing terminates. If no table is found, DrawRing initializes two fictitious atoms f1 and f2 inside the benzene ring.

DrawRing commences a loop that searches for a next atom b after each atom a (f1 and f2 being treated as the final atoms b of the sequence). For each atom b after a, DrawRing calls the FindNextRing routine of the FindNext Position procedure. FindNextRing positions each atom b, tests for interference with previously drawn structure, and modifies mask values MASK{a} and MASK{b} to reflect the new positioning assignment. The direction of a ring atom b relative to its previously drawn neighbor a is found by a direction variable DR1 having a value 0-7. The value of DR1 represents the number of 45 degree increments taken in a counterclockwise rotational direction from a base line direction DR{a} extending from the preceeding atom a. Once the atom b is drawn using an available direction DR1, a new baseline direction DR{b} is set at 180 degrees from the direction DR1 used to draw the atom b. The next atom is drawn using the new baseline direction DR{b}, and the process repeats. Each baseline direction DR{m} and direction variable DR1 has one of eight values, 0-7. The values for DR{m} and DR1 represent the following table space directions: 0 for east, 1 for north-east, 2 for north, 3 for north-west, 4 for west, 5 for south-west, 6 for south, 7 for south-east.

Draw Molecule sets DR(fa) to an initial value (e.g., DR(fa)=0=East). To find the direction DR1 of the next atom, a NEXTRING (CHOICE, RANK) value is added to the baseline direction DR{fa} using modulo 8 addition. The variable CHOICE corresponds to a selected orientation of the benzene ring having a selected direction of the first atom fa thereon. For each CHOICE selection, there is an array of seven values corresponding to the RANK of each atom in the ring including the two fictitious atoms $f_1$ and $f_2$. There are 0-6 direction CHOICES tested sequentially by DrawRing and FindNextRing. For CHOICE=0 and DR(fa)=0, the ring atom directions are found by an array of NEXTRING (CHOICE) values of (3, 5, 5, 6, 5, 6, 6), as shown in Appendix J. Interpreting this sequence, the second atom of the ring has a NEXTRING (CHOICE, RANK) value of 3 starting from the baseline direction of the first atom (DR{fa}=0). Its direction DR1=0+3 (modulo 8) =3. This is northwest of the first atom. A new baseline direction DR{b} is selected at 180 degrees from DR1 or 3+4 (modulo 8) =7. The third atom in the ring has a NEXTRING (CHOICE, RANK) value of 5 from the baseline direction 7 (southeast) indicating that its direction DR1=5+7 (modulo 8) =4. This is west from the second atom. The new baseline direction DR{c} is 180 degrees from DR1, or 4+4 (modulo 8)=0. The fourth atom also has a NEXTRING (CHOICE, RANK) value of 5 indicating that DR1=0+5 (modulo 8)=5, and that the atom lies in a south-west direction from the third atom. The new baseline direction DR{d} is 180 degrees from DR1, or 5+4 (modulo 8) =1. The fifth atom has a NEXTRING (CHOICE, RANK) value of 6 indicating that DR1=1+6 (modulo 8)=7, and that the atom lies in a south-east direction from the the fourth atom. The new baseline direction DR {e} is 180 degrees from DR1, or 7+4 (modulo 8)=3. The sixth atom has a NEXTRING (CHOICE, RANK) value of 5 indicating that DR1=3+5 (modulo 8)=0, and that the atom lies in an east direction from the fifth atom. The last two NEXTRING (CHOICE, RANK) values, 6 and 6, are used to position the fictitious atoms f1 and f2 in the interior positions of the ring.

If the selection CHOICE=0 cannot be drawn, successive CHOICE arrays will be tried. By way of example, if the baseline direction of the first atom a, DR{fa} =east, CHOICE=0 assumes that the benzene ring is oriented on its side with the first atom fa at the rightmost central position. Thereafter, the orientation positions tried are: (1) upright with first atom at upper righthand position; (2) upright with first atom at lower right hand position; (3) upright with first atom at bottom central position; (4) upright with first atom at upper central position; (5) sideways with first atom at lower righthand position; and (6) sideways with first atom at upper righthand position.

Each direction value DR1 is tested before that value is used to position the next atom b. To illustrate, assume a next atom b after the first atom a is positioned by calling FindNextRing with CHOICE=0, RANK=0 and the baseline direction DR{a}=0. A NEXTRING (CHOICE, RANK) value of 3 is selected. DR1 is equal to DR{a}+NEXTRING {CHOICE, RANK} or 0+3=3. The availability of this direction is confirmed by testing MASK{a}. The test is a logical one in which the value of MASK{a} is compared logically with a direction mask corresponding to the selected direction. MASK{a}, which is formed by eight bits, is initially at value {00000000}. A value MDR{DR1} is a mask at atom a corresponding to the direction of DR1=3, having 8 bits of value 1 except in the DR1 direction. MDR{DR1} thus equals (11111011). MASK{a} is logically ORed with MDR{DR1} to obtain {11111011}. Had the result been a FULLMASK, {11111111}, the program would have returned to DrawRing, the PROCESSLIST would have been cleared of (RANK+1) atoms and a new CHOICE value of 1 would have been tried, resulting in the use of (3, 6, 5, 5, 6, 7, 2) as the values for NEXTRING {CHOICE} in FindNextRing.

In the example above, a FULLMASK does not result, indicating that the direction DR1 selected for atom b is potentially available. However, where RANK=0, the FindNextRing routine does an additional test to determine that the position from the first atom a in the opposite (clockwise) direction is available. For CHOICE values of 0, 3 and 4, this direction has a value of {DR1+2}. For CHOICE values of 1, 2 and 5, 6, this direction has a value of {DR1+3}. Accordingly, this test is performed by the logical equations MASK{a} OR MDR{DR1+2}, for CHOICE values 0, 3 and 4, and MASK{a} OR MDR {DR1+3} for CHOICE values 1, 2 and 5, 6. If a FULLMASK results, the program returns to DrawRing to test the next CHOICE value.

Assuming the above-described tests do not result in an error, the coordinate position POS{b} of atom b is determined by multiplying the coordinates POS{a} of atom a by a rotation/translation matrix R{DR1}. If an atom already exists in that position, an error results and the program returns to DrawRing. Otherwise, the position POS{b} is accepted. MASK{a} is modified using the logical OR operation MASK{a} OR INV (MDR{DR1}) to {00000100}. The values of DR{b} and MASK{b} are set. DR{b} is set to (DR1+4) modulo 8=7 and MASK{b}=MASK{b} OR INV (MDR{DR{b}})={00000000} OR (01000000)={01000000}. The program returns using the above-described procedure. Assuming DrawRing and DrawNextRing successfully draws atoms "a-f" of a benzene ring using an initial baseline direction DR(a)=0 and CHOICE=0, the resultant configuration will appear, as follows:

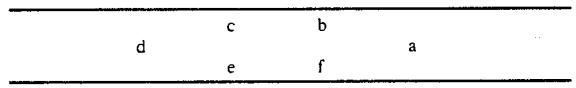

Following the DrawRing routine, the remainder of the Clist is drawn so as to extend to the right of the benzene ring. The baseline direction DR{fa} is set to 4 or west and CList is drawn to the East of the ring. The Draw Molecule procedure calls a DrawList routine which is also part of the FindNext Position procedure.

DrawList first determines whether a Table{a}=Table{a+1} exists in the position of atoms a and a+1. These Tables indicate a case of repeating parentheses and Table (a) is inserted. Otherwise, DrawList tests atom a and a next atom b to determine whether their structures Str{a} and Str{b} TB. If not, the DrawList routine calls the FindNext routine in the FindNext Position procedure. FindNext finds the position of atoms b next to atom a. The directions of the atoms relative to their previously drawn neighbors are found by a second direction variable D2 having a value 0-7 representing the number of 45 degree increments taken in a counterclockwise direction from a first direction variable D1. Direction D2 is found by adding a series of NEXT (CHOICE) values to DR1 until an open direction is found. NEXT (CHOICE)=4 is 180 degrees counterclockwise from the direction DR1; NEXT (CHOICE)=6 is 270 degrees from DR2; NEXT (CHOICE)=2 is 90 degrees from DR1; NEXT (CHOICE)=5 is 225 degrees from DR1; NEXT (CHOICE)=1 is 45 degrees from DR1; NEXT (CHOICE)=3 is 135 degrees from DR1; NEXT (CHOICE)=7 is 315 degrees from DR1; and NEXT (CHOICE)=0 is 0 degrees from DR1.

The value of the first direction variable used to calculate DR2 depends on the baseline direction DR{m} of the previously drawn atom. If DR{m}modulo 2=0, which is true for DR{m}=0, 2, 4, and 6, DR1=DR{m}. Otherwise, DR1=(DR{m}+1)modulo 8 or 45 degrees counterclockwise from DR{m}. This holds true where DR{m}=1, 3, 5 and 7, i.e., where DR{m} extends at a 45 degree angle from the horizontal and vertical directions. Thus, FindNext first tries to draw the atoms in a horizontal or vertical direction. Once an atom is drawn, a new baseline direction DR {m+1} is set at 180 degrees from the value of DR2 used to draw the atom. The next atom is drawn using the new baseline direction DR{m+1}, and the process repeats.

Assuming a first atom a having a baseline direction DR{a}=4, and CHOICE=0, then DR1=DR{a}=4, NEXT{CHOICE}=4, and FindNext calculates the direction of atom b using the equation DR2=(DR°+NEXT {CHOICE}) modulo 8=(4+4) modulo 8 =0, or East. A mask test is performed by means of the logical OR equation MASK{a} OR MDR{DR2}, where MDR is an eight bit mask having bit values of 1, except in the direction DR2. If a FULLMASK results, the value of CHOICE is incremented and a new DR2 is calculated. In the present example, assume Mask{a}={00010000} and MDR{DR2}={11111110}. The result of the logical OR operation is {11111110}. Because DR2 is available, the position of atom b POS{b} may be calculated by multiplying the position of atom a, POS{a} by the translation/rotation matrix R{DR2}. Assuming no atom exists at this position, the value of MASK{a} is changed to {00010001} using the logical OR operation MASK{a}=MASK{a} OR INV (MDR{DR2}). The baseline direction value for atom b DR{b} is set to (DR2+4)modulo 8 =(0+4) modulo 8=4 and MASK{b} =MASK{b} OR INV (MDR DR{b}) ={00000000} OR {00001000}={00010000}. FindNext terminates and the program returns to DrawList to draw the next atom in the list. If there exists an atom of the list indicating a case of pendant parentheses or digital front information, DrawList inserts all tables in PROCESSLIST{i} not previously inserted. DrawList then terminates and the program returns to Draw Molecule. Assuming DrawList and FindNext are able to draw a linear list of atoms "a-e . . ." using an initial baseline direction DR{a}=4 and a value of CHOICE=0, atoms "a-e . . ." will be drawn as follows:

a b c d e . . .

If in DrawList, atoms a and b having Str=TB (triangular bond) are found, DrawTb is called. DrawTB draws a triangular bond between atoms a, b and c. Knowing atoms a and b, DrawTB first finds an atom c connected to atoms a and b. It then initializes a fictitious atom f. In the triangular bond a, b and c, the distance between a and b will be two bond lengths (2bl) to allow atom c to be positioned at the midpoint distance between atoms a and b but at a distance of 1bl from the line connecting a and b. To position these atoms, FindNext (a, f) is first called and fictitious atom f is positioned at a distance of lb from atom a. If FindNext returns an error, the program returns to DrawList and the atoms drawn since the last call to DrawList are cleared from PROCESSLIST. Assuming no error occurs and atom f is drawn, MASK{a} is modified to allow b to use the direction DR2 used for atom f in DrawList. Mask{a} is modified using the logical operation MASK{a}=MASK{a} AND MDR {(DR{f}+4) modulo 8}/ where MDR is an eight bit mask having bit values of 1 except in the direction {{DR{f}+4}modulo 8}. Thus, if DR{a} is 4, Dr{f} is 4 and MASK{a} is {00010001}, then MDR{{DR{f}}+4}modulo 8={11111110} and MASK{a} is freed using MASK-{a}={00010001} AND {11111110}={00010000}. The position bond length of atom a is modified to 2*bl. DrawTB then calls FindNext (a, b). If an error is reported, the program returns to DrawList. Otherwise, DR{b} should be the same as DR{f}, and because the bond length of a is 2bl, the calculated position of atom b, POS{b}, will be 2 bond lengths from atom a in the direction of fictitious atom f. If DR{b} does not equal DR{f}, 2 atoms are cleared from PROCESSLIST and DrawTB is reexecuted. The position bond length of atom a is set back to 1bl.

The direction of atom c from atom a is calculated using the equation DR1=DR{a}+(NEXT{CHID{b}}+CHID{c}+8) modulo 8. CHID represents a direction choice identification variable. NEXT{CHID{b}} is determined from FindNext. The variable CHID is initialized by Draw Molecule to −1 for all atoms in ALLATOM. DrawTB sets CHID{b} to an initial value of 0. Thus, CHID{b} will be 0, NEXT{CHID{b}} will be 4 and CHID{c} will be −1. DR1=DR{a}+(NEXT{CHID{b}}+CHID{c}+8)modulo 8)=4+(4+−1+8)modulo 8=7 or 45 degrees in the clockwise direction from DR{b}. However, because the position bond length of atom a was reset to 1bl, atom c is halfway between and 1bl below atoms a and b. DrawTB tests MASK{a} for interference in the direction DR1 and if full, clears 2 atoms from PROCESSLIST and reexecutes DrawTB. If MASK{a} is not full, and no atom coexists in the selected direction, POS{c} is assigned to atom c. DrawTB then calculates a second direction DR2=(DR1+2*CHID{c}+8) modulo 8. With DR1=7, and CHID{c}=−1, DR2=(7+2(−1) +8) modulo 8=5, or 90 degrees in the clockwise direction from DR1. This is the direction required to move from atom b to atom c. DR2 is used to modify MASK{b} in accordance with the logical OR operation MASK{b} =MASK{b} OR INV(MDR{DR2}), where MDR{DR2} is an eight bit mask having bit values of 1, except in the direction DR2. DR1 is used to modify MASK{a} in accordance with the logical OR operation MASK{a}=MASK{a} OR INV (MDR{DR1}). The DrawList completes the triangular bond drawing process by resetting the DR{c} attribute for atom c and filling the positions of atoms a, f and b in MASK {c}. Thus, DR{c}=(DR1+4) modulo 8; and MASK{c} =MASK{c} OR INV (MDR{DR{c}}) OR INV (MDR{DR2}) OR INV (MDR({DR2+DR{c}/2}), where MDR{DR{c}} and MDR{(DR2+DR{c})/2}, are eight bit masks having bit values of 1, except in the directions DR{c} and (DR2+DR{c})/2, respectively. DrawTB terminates and the program returns to DrawList. Assuming atoms a, b and c having Str{m}=TB, and DR{a}=4, DrawTB will draw these atoms, as follows:

| a | b |
|---|---|

-continued

| c |
|---|

When the list has been drawn, the program returns to Draw Molecule. In the Draw Molecule procedure, the program tests whether a second benzene ring is attached at the end of the atom list, and if so, the DrawRing routine is called to determined the position of those ring atoms.

Thereafter, the Draw Molecule procedure commences a BenzeneRing loop that finds lists of atoms not yet drawn that start or end with a benzene ring that is drawn. These atoms are drawn using the DrawList routine and attached to the previously drawn benzene ring. If the list ends with a benzene ring, that ring is also drawn using the DrawRing procedure.

If, among the Clists, there are no lists connected to a benzene ring, the Draw Molecule procedure selects the longest list and jumps to the NoLiString routine. That routine affects the coordinate position of the first atom of the list to (0, 0, bl). It then calls the DrawList routine of the FindNext procedure to draw these linearly aligned atoms.

Following BenzeneRing, or NoListRing, Draw Molecule executes a ListBegin routine. ListBegin attempts to find a list not yet drawn having a first or last atom that is drawn. If such a list if found, the atoms are drawn using the DrawList routine. If the list ends with a benzene ring the DrawRing routine is used and the BenzeneRing routine thereafter.

If there are no lists not drawn having a first or last atom that is drawn, or, if no Clists are found at the start of Draw Molecule, the Neighbor loop is commenced.

The Neighbor loop looks through the listing of atoms initially classified in decreasing order by their number of connections in ALLATOM. The Neighbor loop searches through the ALLATOM list until it finds an atom that has been drawn. If none have been drawn, a New routine is called that affects the coordinates of the first atom in ALLATOM to (0, 0, bl), and then calls the DrawRing routine if the first atom is part of a benzene ring, and the DrawNeighbor routine if the first atom in the atom list is not part of a benzene group. Following New, or if the atom list considered in Neighbor included a previously drawn atom, the procedure calls a DrawNeighbor routine in the FindNext Position procedure. The DrawNeighbor routine determines the coordinates of all atoms that have not yet been drawn that are connected to an identified drawn atom. The DrawNeighbor routine first attempts to insert a table for the considered atom a. In cases where the neighboring atom b is part of a benzene ring or a Clist, DrawNeighbor calls FindNext to draw the atom b. The program then returns to Neighbor. In Neighbor, if Str {PROCESSLIST{i}}=BZ (last atom drawn), the ring is drawn by DrawRing and the process returns to the BenzeneRing loop. If Str {PROCESSLIST{i}}=LL, the list is cut into two lists starting at the last drawn atom. Both Clists are drawn using DrawList. If one ends in a benzene ring, the ring is drawn using DrawRing. DrawList is then called for the new PROCESSLIST{i}. If, after DrawList, Str {PROCESSLIST{i}}=BZ, DrawRing is again called. If a ring was drawn, the process returns to the BenzeneRing loop; otherwise the process returns to ListBegin.

If in DrawNeighbor Str{a}=TB and DrawTB Str{b}=TB, Drawing is called. If in DrawNeighbor the atom b adjacent the drawn atom a is a member of an ethyl group, the DrawNeighbor routine calls a DrawET routine that determines the correct position of the undrawn atoms forming the ethyl group. DrawET draws an ethyl group where a is drawn, b is a carbon of the group and Str{b}=b. If a carbon atom of structure ET has an inliaison, the inliaison is replaced by a fictitious atom f. DrawET first attempts to insert a Table{b} connected to atom a at the fictitious atom connected to b in TABLE{b}. If such a Table is found DrawET terminates.

DrawET finds the positions of 5 atoms b, c, d, e and g extending from the first atom a. It determines their positions using a FindET routine that tests up to 10 CHOICES of NEXTET {CHOICE, RANK} having 5 values for each atom.

Each atom is drawn and its position tested using MASK values in a manner similar to FindNextRing, FindNext and DrawTB. Thus, starting from a baseline direction for atom a, DR{a}, a direction DR1 is calculated using a NextET {CHOICE, RANK} value in the equation DR1=(DR{a}+NextET {CHOICE, RANK} modulo 8. MASK{a} is then tested using the logical OR operation MASK{a}=MASK{<} OR MDR{DR1}, where MDR{DR1} is an eight bit mask having bit values of 1 except in the direction DR1. The position of atom b is POS{b}, selected by multiplying POS{a} by a translation/rotation matrix R{DR1}. MASK{a} is then reset using the logical operation MASK{a}=MASK{a} or INV (MDR{DR1}). The atom b attributes are set to DR{b}=(DR1+4) modulo 8 and MASK{b}=MASK{b} OR INV(MDR{DR{b}}).

DrawET selects the CHOICE and RANK values used by FindEt in drawing the atoms b-g. Starting from a value of CHOICE=0, and assuming DR{a}=0, atom b is drawn by calling Find ET (a, b, 0, 0). In FindET, this corresponds to a NEXTET value of 5, such that DR1=(0+5) modulo 8=5, and atom b is 225 degrees counterclockwise from DR{a}=0 degrees. Draw{b} is set to (DR1+4) modulo 8=1. DrawET then finds a undrawn atom c of Str{c}=ET, connected to b by calling FindET (b, c, 0, 1). in FindET, this corresponds to a NEXTET value of 3, such that DR1=(1+3) modulo 8=4, and atom c is 135 degrees counterclockwise from DR{b}=45 degrees or 180 degrees from Dr{a}=0 degrees. DR{c} is set to (DR1+4) modulo 8=0. DrawEt then searches for an undrawn atom d connected to b. If not found and b has an inliaison>0, the inliaison is decremented and a fictitious inliaison atom f is initialized. It is assumed that an atom at insert table will be later positioned at f. DrawET then finds the position of atom d connected to b by calling FindEt (b d, 0, 2). In FindEt, this corresponds to a NEXTET value of 6, such that DR1=(1+6)modulo 8=7, and atom d is 270 degrees counterclockwise from DR{b}=45 degrees or 315 degrees from DR{a}=0 degrees. DR{d} is set to (DR1+4)modulo 8=3. DrawET then searches for an undrawn atom e connected to atom c. If not found and inliaison {c}>0, a fictitious inliaison atom f is connected to c at the position of atom e. DrawET then finds the position of undrawn atoms e and g connected to c. If atom g is not found and inliaison {c}>0, a fictitious inliaison atom f is connected to c at the position of atom g. The process assumes that atoms marked cis and trans are on the same or opposing sides, respectively, of the double bond connection between the carbon atoms.

If any call to FindET results in an error, a BACKTRACK procedure is called that clears 1-4 atoms from PROCESSLIST and reexecutes DrawET using a new CHOICE value. Assuming DrawET successfully draws atoms b-g using CHOICE=0 and DR{a}=0, the resultant cis and trans configurations will appear, as follows:

| e   a | g   a |
|---|---|
| c b | c b |
| g   d | e   d |
| cis(a,e), trans(a,g), null | trans(a,e), cis(a,g) |

Following DrawET, the program returns to DrawNeighbor. In the event of an error in DrawNeighbor, a Backtrack routine is called for error recovery. Thus, DrawNeighbor attempts to draw the atom adjacent to atom a. If a is not in a structure, all atoms drawn are cleared and a new position for a is found. Otherwise, if the position of atom a cannot be modified, a Resolve Conflict routine finds a position for atom b corresponding to the position of an adjacent atom c. A new position for c is found. Following the DrawNeighbor and Neighbor loops, when all atoms are drawn, the Draw Molecule procedure terminates.

The chemical string has now been completely defined by the position of its atoms in an atom list and their connectivity in a connectivity table. The atom list and connectivity table information are then translated into the graphics coordinate system of the graphic structure and combined with that structure in the interpret formula routine.

Having reference now to the program flow diagram of FIG. 12, and the state machine diagrams of FIGS. 13 and 14, the String Recognition program will be discussed in greater detail in connection with the following examples:

EXAMPLE 1

C6H5(OH)

Following program initialization and the Input-String procedure, the string C6H5(OH) is input to the Separate routine. Starting from the zero state, and with the GSTACK set to empty, the program reads the character "C", recognizes it as an uppercase character and not front information, and performs a Readstring action on the entire string C6H5(OH). The state machine changes to state 7.

During the Readstring operation, the character string C6H5(OH) is input first to the Treat-One-String program. This routine searches for elementary substrings of the type S0, which are defined by the routine as being disposed between parentheses. Thus, the Treat-One-String program identifies the elementary substring OH in the string C6H5(OH). The program separates the (OH) elementary substring as a partial string to treat (TST) and replaces the elementary substring by a "." in the whole substring (WST) to form "C6H5.".

The program then tests the partial string TST to determine whether there are any existing "." therein, meaning that there exists elementary substrings within the elementary substring TST for which connectivity tables have already been generated and which are identified by an array of pointers WT. If such elementary substring connectivity tables have already been created, the program creates an array of pointers PT formed by the last connectivity tables in WT and deletes them from WT. The connectivity tables represented by PT will be subsequently combined with the connectivity table for the substring TST and the combined table added in WT.

With respect to the elementary substring OH, there are no previously existing elementary substrings already treated. The next instruction is to create a connectivity table for TST. The program thus jumps to the Create-Stack routine with the string OH as input. The Create-Stack program parses through the elementary substring, one character at a time. The output is a stack with all atoms composing the molecule, together with the atoms' valence, structure group type, in and outliaison information and the indice of any connectivity table to insert based on an inliaison with another substring.

Applying these actions to the elementary substring OH, the state machine first initilizes itself to the zero state. The routine then reads the uppercase "O". A "push" action is performed. The "O" character is pushed on the stack together with its valence information, which for oxygen is 2. The state machine then changes to state 1. The program reads the character "H". This causes the program to take the action "push," wherein the character "H" and its most likely valence (i.e., $-1$ for hydrogen) are pushed on the stack. The state machine then changes to state 3 and the program reads the final character of the elementary substring, "null". Upon reading this character, the program performs an "addpush" operation wherein the "H" element is pulled from the stack, and its $-1$ valence is combined with the valence $+2$ for oxygen. The resulting $+1$ valence is associated with the oxygen atom "O." The state machine then changes to state 1. At this point, since there are no further characters of the elementary substring OH, the state machine changes to state 8. Because the elementary substring OH is known to be part of a larger substring, an inliaison value of 1 is added to the first element in the stack whose valence is greater than 1 (or equal to 1 if reduced to 1 atom), in this case oxygen. The inliaison information indicates that the oxygen connects the OH substring to the remainder of the string. The Create-Stack routine then terminates and the Find-Group routine commences operation. The stack output of the Create-Stack routine is as follows:

| At | Val | Str | Il | Ol | Nt |
|----|-----|-----|----|----|----|
| 0  | 1   | /   | 1  | 0  | /  | where "At" identifies the atom, "Val" is the valence, "Str" is the group type, Il is the inliaison value, Ol is the outliaison value and Nt is a "next table" pointer to any previously created elementary substring table.

The purpose of the Find-Group program is to modify the stack created during the Create-Stack program in accordance with the nature of the group and any front information existing in the GSTACK. The Find-Group routine tests for the presence of a "group" by searching for duplicated carbons (i.e., duplicated by a "repeat" action in the Create-Stack routine). In the case of the OH elementary substring, the Find-Group program terminates without modifying the stack once it determines that OH does not contain a repeating carbon "group."

The program then executes the Connect Routine, which generates a connectivity table $T_0$ for the elementary subgroup OH. Because there is only one non-hydrogen atom, i.e., oxygen, there is only one molecule in the connectivity table $T_0$, as shown below:

| $T_0$ | O |
|-------|---|
| O     | / |

The program then executes the Test routine. Because there is only a single non-hydrogen atom in the elementary substring OH, the Test routine results in an "ok" output and the program returns to the Treat-One-String routine. The Draw Molecule procedure is called. Because no benzene rings or Clists are found, the Neighbor routine searches for an atom already drawn. Because there are no drawn atoms, the procedure jumps to New where the coordinates of "O" are determined to be (0, 0, bl). The procedure then calls DrawNeighbor, where no adjacent atoms to "O" are found. A counter p is set to p+1 and the program exists Draw Molecule and returns to Treat-One-String.

In the Treat-One-String routine, the program searches for previous connectivity tables PT to combine with the Table $T_0$. Since there are none, the program adds a pointer to $T_0$ in the last position in WT. Since the whole string is not empty, the program returns to the start of the Treat-One-String routine to treat the whole string "C6H5".

Having input the whole substring C6H5., the Treat-One-String routine determines that there are no remaining elementary substrings. The program then jumps to the Create-Stack program with the string "C6H5." as input.

The Create-Stack program begins with state zero and reads initially the first carbon "C". The action taken by the Create-Stack routine is to push the carbon atom onto the stack, together with its valence $+4$, and to change the state of the state machine to state 1. The program next inputs the digit 6, pushes that digit onto the stack and changes the state machine to state 7. The program then reads the hydrogen atom "H" and commences a repeat action which pulls the last element of the stack (i.e., the character "6"), duplicates the previous character "C" five times to form $C_1$, $C_2$, $C_3$, $C_4$, $C_5$ and $C_6$, and pushes the H and its $-1$ valence to the stack. The state machine changes to state 3. Upon reading the next character of the substring, i.e., "5", the program commences an "addnewval" action which combines the value 5 with the $-1$ valence of the H to change that valence to $-5$. The state machine changes to state 4. The next character input into the Create-Stack program is the '.' previously generated by the Treat-One-String program and representing the elementary substring (OH) previously treated. In response to this input, the program executes a combinlia action which calls addpush. Addpush causes the last element of the stack, H, to be popped and its $-5$ valence to be added to the valence of the last carbon $C_6$ such that the resultant valence of that carbon is $-1$. A "(" is pushed to the stack. Then the atom "O" from table $T_0$ in WT is pushed to the stack, together with a pointer to $T_0$ and a valence 1 equal to the inliaison value. The ")" character is then pushed to the stack. The state machine changes to state 5, and following input of a null character, a suppush action is performed that deletes "(" and ")" from the stack. The new state is 1. No new characters are found in the string and the Create-Stack routine terminates. The resultant stack is as follows:

| $A_t$ | Val | Str | Il | Ol | Nt |
|---|---|---|---|---|---|
| $C_1$ | 4 | | 0 | 0 | / |
| $C_2$ | 4 | | 0 | 0 | / |
| $C_3$ | 4 | | 0 | 0 | / |
| $C_4$ | 4 | | 0 | 0 | / |
| $C_5$ | 4 | | 0 | 0 | / |
| $C_6$ | −1 | | 0 | 0 | / |
| O | 1 | | 0 | 0 | $T_0$ |

The program then executes the Find-Group routine. This routine changes the carbon valences to their initial valence table values +4. The Find-Group routine then determines that the number of carbons equals six and therefore identifies the substring as a benzene or phenol ring. The "Benzene Ring" portion of the Find-Group routine tests the number of hydrogen atoms in the C6H5 substring. Finding that the number of hydrogens (NH) equals 5, the routine changes the valence of $C_1$–$C_5$ from +4 to +3 to reflect the attachment of one hydrogen to each carbon, and adds double and single bond connectivity information to the stack. The valence of C6 is not changed because no hydrogens are attached to that carbon. The Find-Group routine then terminates having generated a modified list of the six carbon atoms and the single oxygen atom together with updated valence and structure information. The resultant modified stack is as follows:

| $A_t$ | Val | Str | Il | Ol | Nt |
|---|---|---|---|---|---|
| $C_1$ | 3 | BZ | 0 | 0 | / |
| $C_2$ | 3 | BZ | 0 | 0 | / |
| $C_3$ | 3 | BZ | 0 | 0 | / |
| $C_4$ | 3 | BZ | 0 | 0 | / |
| $C_5$ | 3 | BZ | 0 | 0 | / |
| $C_6$ | 4 | BZ | 0 | 0 | / |
| O | 1 | | 0 | 0 | $T_0$ |

The program then executes the Connect routine to generate a connectivity table $T_1$ comprising the atoms $C_1$–$C_6$ and 0 from the modified stack generated by the Find-Group routine. A first pass through the stack connects all atoms of valence 1 to the previous atom if possible. In this case, 0 is connected to the last C, C6. A second pass connects the carbons in accordance with the group structure connectivity information (BZ) in the stack. Thus, single and double bonds are added between the carbons at the appropriate locations. A third pass connects any remaining unconnected atoms. In this case there are no such atoms.

The connectivity table $T_1$ is as follows:

| $T_1$ | $C_1$ | $C_2$ | $C_3$ | $C_4$ | $C_5$ | $C_6$ | O |
|---|---|---|---|---|---|---|---|
| $C_1$ | / | 2 | | | | 1 | |
| $C_2$ | / | / | 1 | | | | |
| $C_3$ | / | / | / | 2 | | | |
| $C_4$ | / | / | / | / | 1 | | |
| $C_5$ | / | / | / | / | / | 2 | |
| $C_6$ | / | / | / | / | / | / | 1 |
| O | / | / | / | / | / | / | / |

The Test routine determines that all atoms are fully connected and are in one set. The Draw Molecule procedure classifies the carbon atoms in the string in decreasing order based on the number of connections to other atoms. The atoms are placed in ALLATOM. The selected order is $C_6$, $C_1$, $C_2$, $C_3$, $C_4$, $C_5$. No Clists are found and the Neighbor routine is called. Because no previously drawn atom is found in the string, the New routine is performed. The first atom considered, fa, is $C_6$. Its coordinates are set at $C_6$(0,0,bl). Because $C_6$ is an element of a benzene ring DrawRing (C6) is called using the first direction choices (3, 5, 5, 6, 5, 6, 6), C1, C2, C3, C4 and C5 are drawn, at the following coordinates: $C_1$ (−bl, +bl, bl), $C_2$ (−2bl, +bl, bl), $C_3$ (−3bl, 0, bl), $C_4$ (−2bl, −bl, bl) and $C_5$ (−bl, −bl, bl). The string is arranged as follows:

| | | $C_2$ | $C_1$ | | |
|---|---|---|---|---|---|
| | $C_3$ | | | $C_6$ | |
| | | $C_4$ | $C_5$ | | |

When the ring is drawn, DR{$C_6$} is set to 4 and Draw Molecule returns to the Neighbor loop. The atom counter p is equal to 0. The Neighbor loop calls the Draw Neighbor routine. The first atom drawn with neighbors that are not all drawn is $C_6$. The neighbors of $C_6$, $C_1$ and $C_5$, are drawn. The neighbor 0 is not drawn. FindNext ($C_6$, 0) is called. 0 is put at coordinates (+bl, 0, bl) using an initial direction DR{$C_6$}=4 (See New). The molecule appears as follows:

| | | $C_2$ | $C_1$ | | | |
|---|---|---|---|---|---|---|
| | $C_3$ | | | $C_6$ | O | |
| | | $C_4$ | $C_5$ | | | |

Because there are no further undrawn neighbors of $C_6$, the program returns to Draw Molecule in the Neighbor loop. All neighbors of $C_6$, $C_1$, $C_2$, $C_3$, $C_4$, and $C_5$ are drawn. The program calls DrawNeighbor for 0. Table {0} is not null. Insert Table {0} is called. Insert Table translates the "0" of T0 at position (0, 0, bl) to the position (+bl, 0, bl). Because there is only one atom in T0, no conflict is found and "0" in T1 will have the position (+bl, 0, bl). The Insert Table routine ends. Because there are no undrawn neighbors of "0," DrawNeighbor ends. Because there are no further atoms to draw, the Draw Molecule procedure ends. Following the Draw Molecule procedure, the 1×1 dimension table T0 is added to the connectivity table T1 and the stack is modified to remove the pointer to T0. The Connect routine then terminates and the test routine commences. The Treat-One-String program terminates after attempting to operate on an empty string.

The program then returns to the Separate routine, whereupon the program ends because the input string is now empty.

EXAMPLE 2

2-cis-C2H2Cl,C3H7

Following program initialization and the Input-String procedure, the string is input to the Separate routine. With the state machine set to state 0 and the GSTACK set to empty, the program first reads the digit 2. The action taken is to push the 2 onto the GSTACK and change the state machine to state 1. The next character read is the '−'. No action is taken in response to this character, but the state machine changes to state 2. The next characters read represent the lower case "c" in the notation 'cis.' The action taken is readinfo, which causes the cis notation to be pushed onto the GSTACK. The state machine changes to state 3. The next character read is the '−', in response to which no action is taken, but the state machine changes to state 4. The next character read is the upper case C representing a carbon atom. The action taken is readstring, which causes the program to read the entire substring, C2H2C1, and input that string to the Treat-One-String, Create-Stack, Find-Group, Connect and test routines. The state machine also changes to state 5. The GSTACK is as follows:

|      |
|------|
| cis  |
| 2    |
| NULL |

The first routine, Treat-One-String, searches for but will not find any elementary substrings (i.e., substrings within parentheses).

The substring C2H2C1 is in elementary form and is next input to the Create-Stack routine. With the state machine set to state 0 and the stack set to empty, the Create-Stack routine first reads the character "C" representing carbon. The action taken is to push the character "C" and its most likely valence (i.e., +4) onto the stack. The state machine changes to state 1. The program next reads the digit 2. The action taken is to push the 2 character onto the stack and to change the state machine to state 7. The next character read is the "H" representing hydrogen. The action taken is repeat, which pulls the last element from the stack, i.e., the 2 character, duplicates the previous character "C" one time to form $C_1$ and $C_2$, and pushes the H and its $-1$ valence onto the stack. The state machine then changes to state 3. The next character read is the digit 2. The action taken is addnewval, which combines the value 2 and the $-1$ valence of the hydrogen for a resultant valence of $-2$. The state machine then changes to state 4. The next character read is the "C" of the chlorine atom. The action taken is addpush, which pulls the last element from the stack and combines the $-2$ valence of the hydrogen with the valence $+4$ of the preceding carbon $C_2$ such that the resultant valence for the last carbon is $+2$. The new C is pushed to the stack. The state machine changes from state 4 to state 1. The final character of the substring is the "1." The action taken is pushlow, which combines the character "1" with the last element of the stack (i.e., the "C") and obtain a new element cholorine of valence $+1$. The state machine remains in state 1. No new character is found in the string. The next state is 8 and the create-stack routine terminates. Because the string is known to be partial, the first atom of the stack having a valence greater than 1, i.e. Cl, receives an inliaison value of 1. The result of the Create-Stack routine is a list of the carbon and chlorine atoms, their valence and their in- and outliaison values, as follows:

| At    | Val | Str | Il | Ol | Nt |
|-------|-----|-----|----|----|----|
| $C_1$ | 4   |     | 1  | 0  | /  |
| $C_2$ | 2   |     | 0  | 0  | /  |
| $C_1$ | 1   |     | 0  | 0  | /  |

Following termination of the Create-Stack routine, the output thereof is input to the Find-Group routine. The Find-Group routine resets the carbon valences to 4. The routine then recognizes the substring C2H2C1 as a double linear group because there are two carbons. This results in commencement of the Ethyl-Group subroutine. This subroutine determines that the number of hydrogens in the substring equals 2 and confirms that the information on the GSTACK is related to a double linear group. The Ethyl-Group subroutine then pops the "cis" group information from the GSTACK. If the information on the GSTACK is not related to a double linear group, a flag is set indicating that the substring is ambiguous. Thereafter, assuming the substring is not ambiguous, the Ethyl-Group subroutine changes the values of each carbon atom from 4 to 3 to reflect the attachment of one hydrogen to each atom. The subroutine then adds double bond information between the carbons, and the Ethyl-Group subroutine and the Find-Group routine terminate.

The resultant modified stack is as follows:

| At    | Val | Str | Il | Ol | Nt |
|-------|-----|-----|----|----|----|
| $C_1$ | 3   | Cis | 1  | 0  | /  |
| $C_2$ | 3   | Cis | 0  | 0  | /  |
| $C_1$ | 1   |     | 0  | 0  | /  |

The program then executes the Connect routine which generates a connectivity table $T_2$ for the atoms $C_1$, $C_2$ and Cl, as follows:

| $T_2$ | $C_1$ | $C_2$ | $C_1$ |
|-------|-------|-------|-------|
| $C_1$ | /     | 2     |       |
| $C_2$ | /     | /     | 1     |
| $C_1$ | /     | /     | /     |

The program then executes the Test routine which tests the connectivity between the atoms in the table $T_2$.

Following the Test routine, the program calls the Draw Molecule procedure. Draw Molecule classify the atoms in the file called ALLATOM in decreasing order depending on the number of connections to each atom. Thus, ALLATOM will contain $C_2$, $C_1$ and Cl. No Clists are found and Draw Molecule jumps to the Neighbor loop. There being no atoms previously drawn, the program jumps to the New loop. The New loop assigns C1 the first atom in ALLATOM that is not part of an ethyl group to coordinate position (0, 0, bl). DrawNeighbor (C1) is called. In DrawNeighbor, the undrawn neighbor $C_2$ is recognized as a member of an ethyl group. FindET is called and draws $C_1$, $C_2$ and Cl at $C_1(-2bl, bl, bl)$, $C_2(-bl, bl, bl)$ and Cl(0, 0, bl). It creates a fictitious ethyl atom at $(-3bl, 0, bl)$. The string is drawn as follows:

|   | $C_1$ | $C_2$ |    |
|---|-------|-------|----|
| f |       |       | Cl |

Because there are no remaining undrawn neighbors of $C_2$, the program returns to the Neighbor loop in Draw Molecule, which then terminates and the Draw Molecule routine ends.

Following the Draw Molecule procedure, program control returns to Treat-One-String and then to the Separate routine in state 5. The Separate routine reads the first character of the remaining substring ",C3H7". The routine skips the ",", sets the state to 6 and reads the "C." The program executes a Readstring action wherein execution of the Treat-One-String, Create-Stack, Construct-Group, Connect and Test routines commences.

In the Treat-One-String routine, the routine treats the entire string and jumps to the Create-Stack routine.

In Create-Stack, the first action in response to reading the "C" of the substring is to push the "C" onto the stack and to change the state machine to state 1. The routine next reads the digit 3. The action taken is to push the 3 onto stack and change the state machine to state 7. The next character is the hydrogen atom "H". The action taken is repeat, which pulls the character "3" from the stack, duplicates the character "C" two times to create the characters C11, C12 and C13, and pushes the H and its $-1$ valence to the stack. The state machine changes to state 3. The final character "7" causes an addnewval action to be taken wherein the value 7 is combined with the $-1$ valence of the hydrogen character "H" such that the resultant valence for the hydrogen becomes $-7$. The new state of the state machine is 4. A null character is entered and an addpush action is performed by combining the $-7$ valence of H with the valence of C13, causing that character to have a valence of $-3$. Thus, the result of the create-stack routine is to create a stack listing the three carbon atoms and their valences, as follows:

| At | Val | Str | Il | Ol | Nt |
|---|---|---|---|---|---|
| $C_{11}$ | 4 |  | 0 | 0 | / |
| $C_{12}$ | 4 |  | 0 | 0 | / |
| $C_{13}$ | $-3$ |  | 0 | 0 | / |

Following the Create-Stack routine the program commences execution of the Find-Group routine. The input is the stack created by the Create-Stack routine. In the Find-Group routine, the carbon values are reset to their valence table value 4, and the substring C3H7 is recognized as a linear group. Thereafter, the program tests the information on the GSTACK to determine whether it is related to a linear group. The group information remaining on the GSTACK is the digit 2. Because the group is linear, a single bond connection is provided between each carbon. In assigning the hydrogens, the Find-Group routine takes into account the previously assigned carbon bonds, the in- and outliaison values and the group connectivity information. In this case, because the group information consists of the digit 2, the routine recognizes that the second carbon $C_{12}$ will be connected with the previously treated substring as well as other carbons in its own substring, and will keep three valences open for that connection. The valences of $C_{11}$ and $C_{13}$ are thus changed to 1, and the valence of $C_{12}$ is changed to 3, as the hydrogens are assigned to fill up these carbons. The resultant modified stack is as follows:

| At | Val | Str | Il | Ol | Nt |
|---|---|---|---|---|---|
| $C_{11}$ | 1 | Lg | 0 | 0 | / |
| $C_{12}$ | 3 | Lg | 0 | 0 | / |
| $C_1$ | 1 |  | 0 | 0 | $T_2$ |
| $C_{13}$ | 1 | Lg | 0 | 0 | / |

In addition, the atom $C_1$ from the connectivity table $T_2$ (which has an inliaison value of 1) is introduced after $C_{12}$, together with a pointer to $T_2$. If any ambiguity occurs in determining this connectivity, a flag is raised and the user may interact with the program.

The program then commences execution of the Connect routine which creates a connectivity table $T_3$ for the carbons $C_{11}$, $C_{12}$, $C_1$, and $C_{13}$, as follows:

| $T_3$ | $C_{11}$ | $C_{12}$ | $C_1$ | $C_{13}$ |
|---|---|---|---|---|
| $C_{11}$ | / | 1 |  |  |
| $C_{12}$ | / | / | 1 | 1 |
| $C_1$ | / | / | / |  |
| $C_{13}$ | / | / | / | / |

Thereafter, the program commences execution of the Test routine which tests the connectivity of the table $T_3$.

Draw Molecule first transfers the Ethyl structure information to $C_1$, then classifies the atoms in ALLA-TOM as $C_{12}$, $C_{11}$, $C_1$, $C_{13}$. A Clist $C_{11}$, $C_{12}$, $C_{13}$ is found. Their structural information is replaced by the linear designation LL. Draw Molecule jumps to No Listring. The first atom $C_{11}$ is assigned coordinates (0, 0, bl). NoListring then calls DrawList ($C_{11}$). DrawList draws $C_{12}$ and $C_{13}$ using FindNext. The coordinates assigned by FindNext are $C_{12}$ (1, 0, bl) and $C_{13}$ (2, 0, bl) as follows:

| $C_{11}$ | $C_{12}$ | $C_{13}$ |
|---|---|---|

The program returns to DrawLIst and thence to the ListBegin loop in Draw Molecule. No other Clist is found and the Neighbor loop is started with $C_{12}$ as the first atom from ALLATOM. The Neighbor routine calls DrawNeighbor ($C_{12}$). It is determined that $C_{11}$ is already drawn. $C_1$, however, is an undrawn neighbor of $C_{12}$ having ET structure information and a NextTable ($T_2$). Accordingly, FindET is called, followed by InserTable, which makes correspondence with $C_{12}$ and the fictitious inliaison in $T_2$. Translation will be from fictitious inliaison ($-3$bl, 0, bl) to (1bl, 0, bl). The translation matrix T is as follows:

$$T = \begin{matrix} 1 & 0 & +4/bl \\ 0 & 1 & 0 \\ 0 & 0 & 1 \end{matrix}$$

The molecule is drawn as follows:

| $C_{11}$ | $C_{12}$ | $C_1$ $C_{13}$ | $C_2$ | Cl |
|---|---|---|---|---|

No overlapping is detected. $C_{13}$ is the last neighbor of $C_{12}$ and is already drawn. DrawNeighbor terminates and because all atoms are drawn, Draw Molecule ends.

The program then returns to Treat-One-String and the tables $T_3$ and $T_2$ are combined to obtain a complete connectivity table $T_4$ comprising all of the atoms of the string, as follows:

| $T_4$ | $C_{11}$ | $C_{12}$ | $C_1$ | $C_2$ | $C_1$ | $C_{13}$ |
|---|---|---|---|---|---|---|
| $C_{11}$ | / | 1 |  |  |  |  |
| $C_{12}$ | / | / | 1 |  |  | 1 |
| $C_1$ | / | / | / | 2 |  |  |
| $C_2$ | / | / | / | / | 1 |  |
| $C_1$ | / | / | / | / | / |  |
| $C_{13}$ | / | / | / | / | / | / |

The Treat-One-String routine then attempts to read an empty substring. This causes the Treat-One-String routine to terminate and the program returns to the Separate routine. The Separate routine also reads an empty string, at which point the entire program terminates.

As an alternative to the Interpret Formula routine, the character codes obtained by OCR may be reformatted in conformance with the associated images found on the diagram (i.e., COCH3 or C1) and a procedure involved to search through template files stored in memory to see if such a character string is a common chemical substructure (e.g., COCH3). If so, its representation in the template file is rotated, translated, and scaled into place in the molecular structure file. If no template is four d, the program assumes the line to be a simple atom type (e.g., C1). The resulting molecular structure can be visually checked by displaying the chemical structure with commercially available programs.

Figure 10:
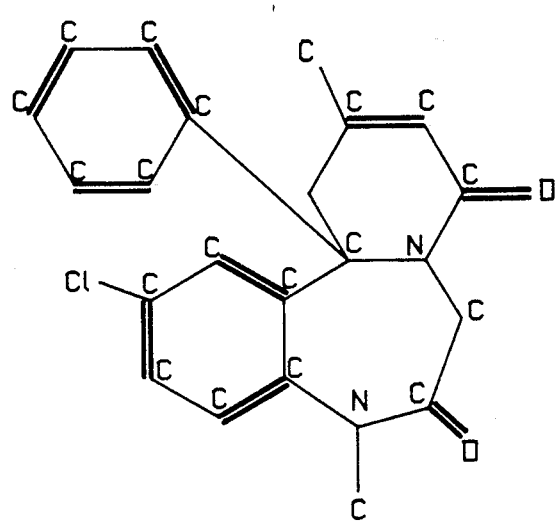
FIG. 10 is a diagrammatic representation of an image after structure recognition.
Figure 11:
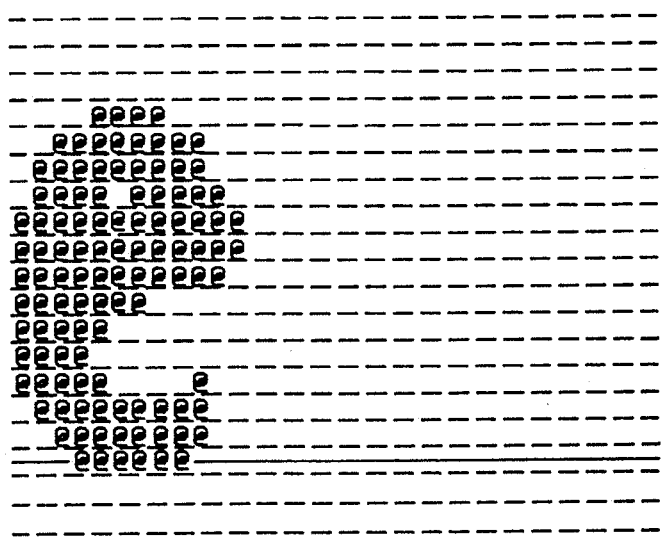
FIG. 11 is a diagrammatic representation of a character cut out and normalized from the source file.

At the conclusion of the Structure Recognition stage, the system has produced all information needed to create a complete molecular structure file, including a list of nodes plus a connection table defining the bonds between nodes. FIG. 10 shows the resultant recognized structure.

I. AGGREGATION

The Aggregation procedure is set forth in detail in pseudocode form in Appendix K hereto. Interpret Formula produces a complete description of the molecule by combining the molecular substructure file created during the Interpret Formula routine with the molecular structure file information previously generated during the Atoms-Recognition and Interpret-Circle routines. Then, the Aggregation procedure forms the completed molecular description of the molecule extract in a required format to be memorized in a file. The Aggregation procedure can be customized to fit various output formats.

J. POST PROCESSING

The memory clean up procedure is shown in detail in pseudocode format in Appendix L hereto. As shown and described therein, a check is made of the validity of the final molecular structure file as a molecule description. Can it be drawn? Does it conform to chemical laws? It is at this stage, moreover, at which modifications and refinements of the software system could be added, for the chemical context permits validity to be checked to an extremely high degree of confidence. If a chemical balance law is violated, for example, indicating an error in the translation process, the structure can simply be displayed on a screen to be completed manually in a graphics editor mode. More complex post-processing, which can also be investigated, would seek to pinpoint the error and propose modifications that might satisfy the validity checks.

Accordingly, a novel procedure for optical recognition of chemical graphics and chemical string parsing has been disclosed having broad applicability in fields that handle chemical publications and databases, such as governmental regulatory agencies, in-house safety departments, chemical marketing industries, and publishers. Although various embodiments have been shown and described, it will be understood that many more modifications may occur to those skilled in the art and the invention, therefore, is not to be limited except in accordance with the spirit of the appended claims and equivalents thereof.

APPENDIX A

SEPARATE DIAGRAM

Pseudocode for separating chemical structure diagrams from a scanned image.

KEY TO SYMBOLS USED:

cc = "connected component", a subimage consisting solely of connected black pixels.

RSI = "rectangular subimage" containing a cc.

P = the scanned image (binary) of a printed page containing diagrams and accompanying text.

L = an index specifying the leftmost column of an RSI of P.

R = an index specifying the rightmost column of an RSI of P.

T = an index specifying the topmost row of an RSI of P.

B = an index specifying the bottommost row of an RSI of P.

D = the (L,R,T,B) indices specifying a RSI of P.

RL = a listing of RSIs, D1, D2, D3,...

CCi = the (L,R,T,B) indices specifying the ith cc of P,
 Thus, CCi = (Li,Ri,Ti,Bi).

S = a set of cc's of P.

w = a threshold on subimage width.

h = a threshold on subimage height.

t = the thickness of search bands to the left and right of an RSI.

v = the height of search bands above and below an RSI.

ASSUMPTIONS OF THE ALGORITHM:

1. Every structure diagram in P contains at least one cc of size at least (h,w) rows and columns.

2. Every cc having size at least (h,w) rows and columns belongs to a structure diagram.

3. A structure diagram is separated from surrounding text by whitespace of more than (v,t) rows and columns.

4. The structure cannot be partitioned into two parts that are separated by whitespace greater than (v,t) rows and columns.

The above conditions have been found to be true for a variety of document types, although w,h,t,v may have to be assigned different values depending on document type as well as on scanner resolution.

ALGORITHM:

Initialize RL to empty.

Find S = {CCi}, the set of all cc's of P.

START.

```
If there is CCi in S such that
    Ri-Li > w  and  Bi-Ti > h

Then
    initialize D to consist of (L=Li,R=Ri,T=Ti,B=Bi)
    remove CCi from S

LOOP.
    If there is CCj in S such that
        CCj intersects the rectangle defined by (L-t,R+t,
        T+v,B-v)
    Then
        modify D such that
          L = min (L,Lj), R = max (R,Rj),
          T = max (T,Tj), B = min (B, Bj).
        remove CCj from S
        go to LOOP
    Else
        add D to list RL
        go to START
Else exit.
```

APPENDIX B
CONSTRUCT GROUPS

Pseudocode to construct groups for a diagram from a scanned image.

KEY TO SYMBOLS USED:

P = "Point", (X,Y, Condition)
    Conditions are Endpoint: only one connection
                       Chainpoint: only two connections
                       Junctionpoint: more than two
                                        connections
                       Circlepoint: element of a circle
V = "Vertex", (X,Y, Status, set of points connected
    thereto)

```
Vector = (BP,EP) begin point, end point
SVectors = set of Vectors
SV = set of Vertices
G = (Xmin,Xmax,Ymax,Ymin,Class,set of vertices in the group)
SG = set of group
```

STARTING CONDITIONS OF THE ALGORITM.

1. The output of the module vectorize produces a set of vectors.

ALGORITHM.

Initialize SV

For all Vector in SVectors if condition of BP is endpoint add a new point in SV
    if condition of BP is junctionpoint and BP does not
      exist in SV add a new point in SV
    if condition of EP is endpoint or chainpoint or
      circlepoint add a new point in SV and add the
      connection between BP and EP
    if condition of EP is junctionpoint
    if EP is not in SV add a new point in SV add the
      connection between BP and EP end of copying the image in memory
grouping phase Initialize SG START.
if find a Vertex V of SV that the status is ungrouped
    create a new group G with a class value = unknown, and
    add this point to G
    add all vertices of (connect to V) in G (see below)

go to START

Else exit.

end grouping phase add all vertices of (connect to V) in G

LOOP
if find a Vertex V1 in connect to V that is ungrouped
add all vertices of (connect to V1) in G
go to LOOP Else exit.

APPENDIX C
CLASSIFY GROUPS

Pseudocode to classify the groups of a diagram from a scanned image.

KEY TO SYMBOLS USED:

V = "Vertex", (X,Y, Status, set of points connected thereto)
G = (gheight, gwidth, Class, set of vertices in the group)
SG = set of group
height = average height of a character
width = average width of a character
ngroup = number of groups
c = number of characters

ASSUMPTIONS OF THE ALGORITHM.

1. The smallest groups formed by a great number of vertices are characters.

2. Bond groups formed by a great number of vertices have one dimension two times bigger than the average dimension of a character.

3. Dots are less than 0.2* character height

4. Small horizontal, less than a character width are minus.

ALGORITHM.

classify all groups as unknown sort the groups formed by more than 3 vertices depending on their height in ascending order.

find first letter, width is less than 3 times its height height = gheight of the smallest group For all group if gheight is less than 2* height
    compute new height (average) (it is a potential
    letter)

sort the previously selected groups depending on their width in ascending order.

width = gwidth of the smallest group

For all groups if gwidth is less than 4* width
    classify the group as Letter
    compute new width (average)
    compute c if c = ngroup, there is no character among the groups with many vertices; go through the groups with a small number of vertices to confirm this result.
For all remaining groups composed of a large number of vertices, classify as bond or circle For all groups composed of less than 4 vertices
    if gheight is > 1.8* height or gwidth is > 1.8* width
      classify as bond if 3 vertices and letter size
      classify as letter if 2 vertices and length is less than 0.2* height
      classify as dot if 2 vertices horizontal and letter size
      classify as minus

APPENDIX D
CREATE STRINGS

Pseudocode to create strings for a diagram from a scanned image.

KEY TO SYMBOLS USED:

G = (gheight,gwidth,X,Y,Class,set of vertices in the group)
SG = set of group
GL = group letter (position=group, meaning)
ST = string set of group letters
S = set of strings

STARTING CONDITIONS OF THE ALGORITHM.

1. The characters are aligned horizontally or vertically.

ALGORITHM.

create an empty set of strings S sort the groups classified as letter or unknown depending on their X coordinate (in ascending order.)

```
For the sorted groups
   find the first letter
   create a new string ST call horizontal_string to find all horizontal letters of
   the same string (see below)

if the number of character in this string is 1, then free
   it (it may be a character of a vertical string)
End For sort the groups classified as letter or unknown depending on
their Y position (in ascending order.)

For the sorted groups
   find the first letter
   create a new string ST
   call vertical_string to find all vertical letters of the
   same string (see below)
End For All remaining groups that are unknown or minus are
classified as bonds horizontal_string:   (find horizontal string related to
                      one character)

find all unknown or minus groups located before the letter
   add a new GL to the string add the original letter as a new GL find all unknown or letter or minus group located after the
letter
   add them as a new GL to the string
``` vertical_string: (find vertical string related to one
character)
find all unknown or minus groups located before the letter
   add a new GL to the string
add the original letter as a new GL
find all unknown or minus group located after the letter
   add a new GL to the string

APPENDIX E
VECTOR CLEANUP

Pseudocode for vector cleanup routine.

KEY TO SYMBOLS USED:

V = "Vertex", (X,Y,Status, set of points connected thereto)
G = (Xmin,Xmax,Ymax,Ymin,Class, set of vertices in the
     group)
SG = set of group

STARTING CONDITIONS OF THE ALGORITHM.

1. If in the drawing there is a broken line, the angle between each segment is more than 30 degrees

ALGORITHM.

Initialize SV

In all group classified as bonds find V0 vertex that is connected to only two other
      vertices V1 and V2
   if angle between V0V1 and V2V0 less than 30 degrees
         remove V0, connect V1, V2 end of making straight connection determine the medium value of bond length

In all group classified as bonds
  find the bond length, if smaller than a threshold,
  delete the medium vertex
  end of Vector Cleanup

APPENDIX F
OCR

Pseudocode for character recognition of a diagram from a scanned image.

KEY TO SYMBOLS USED:

GL = group letter (position=group, meaning)
ST = string set of group letters
S = set of strings
posx,posy = position X and Y of the character in the
    isolated raster image
lposx,lposy = position X and Y of the last character in the
    isolated raster image
COPY, COPY2 = copy of the character cut out from the
    isolated raster image.
AvHeight = Median value of the height of uppercase charact-
    ers, used as reference to determine if there is one or
    two characters.

STARTING CONDITIONS OF THE ALGORITHM.

1. In the isolated raster image the character drawing is continuous

ALGORITHM.

The following algorithm cut out a character from the image
Determine if it is not already treated Depending on its size, separate it in the different character
Then recognize it

```
For all strings of S.
  For all characters of ST.
    from the group information find its location in the
    real image cut out the character from the real image
    following the pixel on into COPY, and get the real
    height in the image
end for AvHeight = median value of the height of these characters For all strings of S.
  For all characters of ST.
    from the group information find its location in the
    real image cut out the character from the real image
    following the pixel on into COPY, and get the real
    position in the image if lposx = posx && lposy = posy
      the character was treated, delete this GL from the
      string ST else
    lposx = posx, lposy = lposy
    depending on the size, determine n number of characters
    glued together
      if n > 1
  GLUED
    find the column of separation.
    duplicate in COPY2.
    create a new GL in the string ST.
    call recognition process of COPY2.
    if n-1 > 1 go to GLUED
call recognition process of COPY.
```

End for all characters
End for all strings

Delete all empty strings.

APPENDIX G
ATOMS RECOGNITION

Pseudocode for atoms recognition for a diagram from a scanned image.

KEY TO SYMBOLS USED:

G = (gheight,gwidth,X,Y,Class,set of vertices in the group)
SG = set of group
GL = group letter (position=group, meaning)
ST = string set of groups letter
S = set of strings
A = atom (V vertex, M meaning)
AL = set of atoms

STARTING CONDITIONS OF THE ALGORITHM.

1. In a structure all atoms that are not expressed explicitly are considered to be "Carbon"

2. All ending points are considered to be adjacent a character within a character size distance.

ALGORITHM.

```
create an empty set of atoms AL
For all strings ST in S
    for all letters GL
    add these letters in AL
    end for
End For
```

```
For all groups classified as bonds
    find all vertices V that are junction points
    add V in AL, with meaning "C"
End For
For all groups classified as bonds
    find all vertices that are end points
        find the closest atom A in AL
            replace V by the position of A
        else add a new "C" atom for V
End For
For all atoms of Carbon not in a string but recognized by
    the structure if their connectivity is greater than four
    flag an error
End for
End of atom recognition.
```

APPENDIX H
INTERPRET CIRCLES

Pseudocode for interpretation of circles as bonds for a diagram from a scanned image.

KEY TO SYMBOLS USED:

G = (gheight,gwidth,X,Y,Class, set of vertices in
    the group)
SG = set of group
A = atom (V vertex, M meaning)
AL = set of atoms
R = ring, set of vertices related to one ring (group
    of type CIRCLE)
RL = ringlist set of all rings R
W1,W2,LastW = vertices of rings
TW = set of Wi that are in 3 rings
DW = set of Wi that are in 2 rings
STARTING CONDITIONS OF THE ALGORITHM.

1. Circles are benzene groups

ALGORITHM.

```
create an empty set of rings RL
create an empty set of vertices related to one ring R Classify the groups that are CIRCLES by their x position
For all groups G in SG
      if the Class of G is CIRCLE
         find the ring R of vertices in the atomlist AL
            that surrounds the circle G
         add it in RL
End For to find the rings create an empty set of TW Among the rings, find all vertices W in common within
      3 rings
add them to TW
for all W1 not fully bound in TW
      Second = TRUE
      START
         find a next vertex W2 not fully connected in TW
            add Second bond W1 W2
            W1 = W2
            Second = not Second
      GO TO START
End for all W1 if all W1 in TW are fully connected go to SINGLE-DOUBLE-RING
create an empty set of DW for all W1 not fully connected in TW
find W2 one next vertex of W1 not fully connected
   add TRUE bond W1W2
   add W2 in DW
End for all W1
```

```
for all W1 in DW
   Second = FALSE

CONTOUR
     if not find W2 = next vertex of W1, not fully connected
on the contour and not in DW End for All W1 else
        if find W2 = next vertex of W1, not fully
        connected on the contour and not in DW
           mark R2 ring of W2 used
           add Second bond W1 W2
           W1 = W2
           Second = not Second
Go to CONTOUR SINGLE-DOUBLE-RING
     for all ring not used
       Find W1 a point on the contour
       LastW = W1
       Second = TRUE
   SINGLE-CONTOUR
     if not find W2 = next vertex of W1, on the contour
        different of LastW
          Go to SINGLE-DOUBLE-RING
     else
        if find W2 = next vertex of W1, on the contour
           different of LastW
      mark R2 ring of W2 used
        add Second bond W1 W2
        W1 = W2
        Second = not Second
     Go to SINGLE-CONTOUR
end for
end interpret_circle.
```

APPENDIX I

INTERPRET FORMULA

Key to Symbols Used:

AL = set of atoms in the graphic space
TABLE = connectivity table of atoms in the table space
GOut, GOut1, GOut2 = outliaison atoms in the graphic space
TOut, TOut1, TOut2 = outliaison atoms in the table space
FROM(m) = atom used to determine the position for atom m
POS(m) = (x, y, bl) position of atom m and its bond length
CHID(m) = direction choice used to position atom m
S flag used to insert a table.
gd, td = distance in the two spaces
Gangle, Tangle = angle between the horizontal axis and a line in the two spaces Assumptions of the Algorithm 1. A maximum of two connections between the bond structure and the string is possible. Otherwise, the intervention of the user is required.

Algorithm

```
create a string to send to interpret formula
If the string is not useful (no outliaison)
      find another string above or under that is useful
      add the corresponding connection
      if none discard this string
end If Call Formula String Processing (see pseudocode in
      Appendix J)
      (output is a connectivity table with fictitious
      outliaison atoms)
In AL create memory for all atoms of the connectivity table
Add the corresponding connections
```

If one outliaison

```
BEGIN
For all atoms in TABLE do
     Translation (POS(GOut) - POS(TOut))
     Define rectangle circumscribing the atoms of the table
     S = 0

LOOP
If there exists no points of the graphical structure inside
     the rectangle and there exists no bond intersecting
     an edge of this rectangle
     go to END
For all atoms in TABLE and the rectangle do
     Symmetry (axe X = x component of POS(GOut))

If there exist no points of the graphical structure inside
     the rectangle and there exists no bond intersecting an
     edge of this rectangle
     go to END
     For all atoms in TABLE and the rectangle do
     Symmetry (axe Y = y component of POS(GOut))

If there exist no points of the graphical structure inside
the rectangle and there exists no bond intersecting an
     edge of this rectangle
     go to END
     For all atoms in TABLE do
        if S = 0, Rotation (90 degree), S = 90, go to LOOP
        if S = 90, Rotation (45 degree), S = 45, go to LOOP
        if S = 45,
             if FindNext (FROM(TOut), TOut) = error, see user
             (see FindNextPosition procedure of pseudocode
             below for FindNext routine)
             go to BEGIN
```

If two outliaisons

```
gd = distance (GOut1, GOut2)
td = distance (TOut1, TOut2)
FIT
if gd/td < 0, symmetry (around the median of TOut1, TOut2)
if gd/td < 0.7 or gd/td > 1.4 if FindNext (FROM{TOut1},TOut1) = error
CHID{TOut1} = 0
if FindNext (FROM{TOut2},TOut1) = error, see user
else go to FIT
else go to FIT end If
    For all atoms in TABLE do
        Scale (gd/td)
    Define rectangle circumscribing the atoms of the table
    Gangle = angle (GOut1, GOut2)
    Tangle = angle (TOut1, TOut2)

For all atoms in TABLE and the rectangle do
        Rotation (Gangle-Tangle)
        Translation (POS{GOut1} - POS{TOut1})
    S = 0

If there exists no points of the graphical structure inside
    the rectangle and there exists no bond intersecting an
    edge of this rectangle
    go to END REDO
If S < 9
    Symmetry (around axe TOut1, TOut2)
    If there exist no points of the graphic inside the
        rectangle and there exist no bond intersecting an
        edge of this rectangle
        go to END

S = S + 1
```

Translation (parallel to a line perpendicular to
   Out1, GOut2 of (+-)S*b1/2)
If there exists no points of the graphic inside the
   rectangle and there exist no bond intersecting
      an edge of this rectangle
         go to END
      else go to REDO else See user END
   Insert the new atom positions
   end of Interpret-Formula

APPENDIX J
FORMULA STRING PROCESSING

Pseudocode for formula string processing of unknown molecule strings.

Grammar assumptions for all string processing
The following conventions are common to all the string processing routines:

Naming Conventions:
    U = Upper case + '.' + '='
    l = lower case
    d = digit
    s =    '+' + '-'
    p1 = '('
    p2 = ')'
    e = '-' separator
    c = ','

In and Outliaison
'.' and '=' are characters used during the processing to memorized inliaison and outliaison. An outliaison is a connection between an atom of the molecule and another that is not in the string. Typically, this type of connection is between an atom of the string and the graphical structure that is connected to this atom. In the input string this type of connection is represented by a '=' and follows directly the atom that is involved. An inliaison is a connection between two elementary substrings of the same string. During processing each elementary substring is treated separately and then replaced by '.' in the string.

String Definitions

The chemical string processing routine recognizes several different string types, those being S0, S1, S2, S4, S5 and S6.

- S0 = U(U+l+d+s)*   (COHCl2-; CHCl-2)

S0 starts with an upper case character followed by any or many characters chosen among upper, lower case, digit or sign. S0 does not contain '(' or ')'. S0 is called an elementary substring. The symbol "*" means that the string elements may be repeated zero or more times. The symbol '+' means one character of the type in parentheses. In the S0 substring, all characters have the same role, no superscripts or subscripts are used.

- S1 = (S0+p1S0p2)(d+s)*S1*
      (CH4; (CH3)2; (CH2)-2; C3H5(CH3)3)

S1 is of the form S0 or S0 within parenthesis followed by any or many digits or signs. This format can be repeated several times. S1 is called a substring.

- S2 = ll*eS1   (cis-C2H2Cl2)

S2 is a substring preceded by front information. In S2 the front information reports directly to the substring S1 and is composed only of one or more lower case characters.

- S3 = S1+S2+p1(S1+S2)p2d    ((cis-C2H2Cl)2)

S3 is not a chemical string on its own, it is an intermediate step to build a more complex string.

- S4 = (dc)*dcdeS3cS1    (1,3-(cis-C2H2Cl)2,C5H10)

S4 includes digital front information and two substrings, the first is of the type S3, the second is of the type S1. One of the front information digits refers to the connection of valence one between S3 and S1. The other reports the position in S1 at which S3 is connected.

- S5 = (de(S1+S2)c)*S1    (1-CH3,3-cis-C2H2Cl,C5H10)

S5 is an S1 substring preceded by any or many strings starting with digital front information. The digit reports the position of the connection in the last substring S1.

- S6 = (((dc)*dcdeS3c)*+(de(S1+S2)c)*)*S1
       (1,4-(CH3)s,3-cis-C2H2Cl,C5H10)

S6 is a combination of S4 and S5.

Substring Grouping

A chemical string to be processed must be recognized by the grammar, but all strings recognized by the grammar may not be a valid chemical string. Thus, ApH2 may not be valid because Ap is not an atom. This example will be valid only if Ap is defined as a compound by the user in the valence table. In addition, certain assumptions about molecular structure can be applied by classifying a chemical string into a known group type. The chemical string processing program herein utilizes three such groups.

1. Linear Group S1CxHkA$_i$d$_i$S1
       where:

S1 may be empty;

x is the number of carbon atoms, $x > 2$ and x not equal to 6;

$A_i$ is another element or combined atoms valence $(A_i) = 1$, for example: (CH3) OH;

$sum(d_i) + k >= maxi(4,x)$;

or $x = 2$ and S1 is not empty.

2. Cycle group Benzene S1C6HkAidiS1

Where:

Ai is another element or combination of atoms valence (Ai) = 1, for example: (CH3) OH; $sum(di) + k >= 6$ Cycle groups having a number of carbons different from 6 are not allowed (They need to be drawn);

Cycle groups formed by 6 carbons are assumed to be of the benzene type (They need to be drawn);

Linear groups of 6 carbons are only allowed in the following cases: C6Hx and C6Ax Where:

$x > 6$ and $val(A) = 1$.

3. Double Linear Group a.  cis-C2H2S1 or trans-C2H2S1 b.  C2HkA$_i$d$_i$

Where:

$A_i$ is another element or combination of atoms of valence $(A_i) = 1$, for example, (CH3) OH;

$sum (d_i) + k = 4$.

If $sum (d_i) + k > 4$, the string is treated as a linear group.

4. Sulfur Compound S1SOxS1 a.  $x = 0$, valence of S = 2.

b.  sulfinic: $x = 1$, valence of S = 4, double bond between S and O.

c.  sulfinic: $1 < x < 5$, valence of s=6, double bond between S and a maximum of two Oxygens and single bond with the others.

5. Nitrogen compound valence of N = 3 a.  S1NOx $x = 1$, double bond between N and O x = 2, the compound is interpreted as S1(N+)(O-)O: double bond between N and one O, single bond between N and the second O and single bond between N and S1.

b.  S1Nx x = 2, double bond between the two Nitrogen x = 3, the compound will be interpreted as S1N(N+)(N-), with double bonds between the linear chain of Nitrogen's and single bond between S1 and one Nitrogen.

Front or Group Information

1. Accepted i, iso = Isolated for linear groups n = normal for linear groups s, sec = second for linear groups t, tert = tert for linear groups cis, trans for double linear groups p, para = para for benzene rings m, meta = meta for benzene rings o, ortho = ortho for benzene rings digit for rings and linear groups 2. Ignored (l,d)

3. Not accepted (L, D, R, S, CIS, TRANS)

R is sometimes used to represent a substitution of valence 1 and S is an existing atom. L, D, Cis and TRANS may also be interpreted as atoms. In addition, it is difficult to differentiate between "-" the minus sign, and "-" the separator.

Valence Table

1. The valence table is given by the user.
2. The valence table sometimes allows 2 valences for the same atom, each of which is affected by a probability value. If the program fails when creating the connectivity, a next valence will be tried.
3. Predefined compounds can be added (e.g., Me for CH3, Be for C6H5); the compounds may be defined directly with a formula string or indirectly with the name of a molecular structure file.

Restrictions and Assumptions

1. Hydrogen atoms immediately follow the atoms they are attached to, except that they may precede atoms at the beginning of the string.
2. If an atom has a superscript and a subscript, the subscript must precede the superscript, unless parenthesis are used to solve the ambiguity.
    for example: (OH$^-$)$_2$
3. A valence sign is never followed by an integer bigger than 9.
4. An elementary substring between parentheses is an entity of its own, with only the first or last atoms connected to the rest of the string.
5. A substring an entity on its own with only one atom connected to the rest of the string.
6. The connectivity between an elementary substring and the substring is of valence one or two.
7. The connectivity between a substring and the whole string is of valence one.
8. The front or group information refers to the first group in the string that is not in parenthesis.
9. Only the atoms connected to the first carbon of a group may be written before the carbons.
10. Atoms are fully bonded.
11. An atom is usually bonded to its neighbors.
12. If a string is of the form SAdSs (N(CH3)2-) the atoms A have identical roles, and the ending sign cannot report to them.
13. An atom must be connected to another one that is as close as possible to it in the string description.
14. Atoms have no more than two main valences.
15. Only a few atoms in a string have two valences.
16. All atoms A written in the form Ad, have the same valence.

FORMULA STRING ROUTINES

SEPARATE

Pseudocode for the separation of front information from substrings in chemical string parsing.

Types of characters considered:
1. Uppercase
2. Lowercase
3. (
4. )
5. digit
6. separator: '-'
7. coma ','
8. signs '-+'
9. other Key to Symbols Used:
ST = string that is treated
c = character of the string
ctype = character type
State = current state of the state machine
GSTACK = Stack where the front information is pushed down.
Action = Action done in respect of the current state, and the type of the character read from the string.
result = result of the last Action Assumptions of the Algorithm:
1. The type of strings allowed are described in the grammar
    examples { 1-cis-C2H2Cl,3-trans-C2H2Cl,C7H14;
    3,5-(cis-C2H2Cl)2,C7H14}

Algorithm:
State = 0
create an empty GSTACK
For all character c in the string ST ctype = find type correspondence of c
        result = Action on c depending on State and ctype
end for
end create GSTACK States:

The States generated during the Separate routine are shown in Fig. 13.

Actions:
1. Push - push group information to the stack.
2. Readinfo - read the front information and if not ignored or rejected, push the information to the GSTACK.
3. Readstring - read a substring, and treat it with the information from the GSTACK and its related tables.
4. Copytable - create a new connectivity table identical to the last created.

States: The state machine utilized by the separate routine is shown in Fig. 16.

TREAT-ONE-STRING
---

Pseudocode for treating one string in chemical string parsing.

Keys to Symbols Used:

c = character of the string
Number_of_parenthesis = number of balanced parenthesis
WST = whole string
TST = partial string to treat (part between parenthesis)
partial = indicate if the string is complete or partial:
          - NO not partial
          - SS substring (one inliaison at the first atom possible)
          - LS elementary substring on the left of a string (one inliaison at the first or last atom possible)
          - MS elementary substring in the middle of a string followed by a repeating factor (one or two inliaisons at the first or last atom possible)

- RS elementary substring on the right of a string or elementary substring in the middle of a string without repeating factor (one inliaison at the first atom possible)

PT = array of pointers to connectivity tables of elementary substrings treated. These elementary substrings are represented by '.' in TST.

WT = array of pointers to connectivity tables of elementary substrings treated. These elementary substrings were in WST, and will be combined later.

Assumptions of the Algorithm

1. A substring between parenthesis is an entity on its own, with only one atom connected to the rest of the string.
2. An elementary substring between parenthesis is an entity on its own, with only the first or the last atom connected to the rest of the substring.
3. The connectivity between the substring and the whole string is of valence one.
4. The connectivity between an elementary substring and the whole substring is of valence one or two.

Algorithm

For the whole substring controls if the parenthesis are balanced
Number_of_parenthesis = number of elementary substring
START
if find the first elementary substring
    copy in TST
    replace it in WST by '.'
    affect partial to its corresponding value If in TST there are some '.'
(presence of '.', means there exist elementary substring already treated which connectivity tables are pointed by WT)

create PT, formed by the last tables in WT
    delete them from WT create the new connectivity table for TST
    (stack, then table by calling Create_Stack, and
    connect)
(return point from OK)
draw molecule
combine PT with the new connectivity table
add it in last position to WT
else go back to START
end if find elementary substring else create the new connectivity table for WST (stack, then table)
(return point from OK)
draw molecule
combine WT with the new connectivity table
return the table

CREATE-STACK

Pseudocode for creating the stack for chemical string parsing.

The following character types are recognized by the state machine:

1. H
2. Uppercase
3. Lowercase
4. (
5. )
6. digit
7. sign
8. +
9. .
10. other

Key to Symbols used:

ST = string that is treated c = character of the string ctype = character type

State = current state of the state machine

STACK = atom information push-down stack

Action = Action done for the current state, and the character type result = result of the Action Starting Conditions of the Algorithm:

1. All atoms are in the valence table.
2. Hydrogen atoms immediately follow the atoms they are attached to, except that they may preceed atoms at the begininng of the string.
3. If an atom has a superscript and a subscript, the subscript must precede the superscript, unless parenthesis are used to solve the ambiguity, for example: $(OH^-)_2$.
4. A valence sign is never followed by an integer greater than 9.
5. Hydrogen atoms are not saved.

Algorithm:

State = 0 create an empty Stack

For all character c in the string ST ctype = find type correspondence of c result = Action on c depending on State and ctype State = depending on the current State and the ctype if result = COMPOUND create stack for compound end For end Create Stack

STATES

Figure 14:
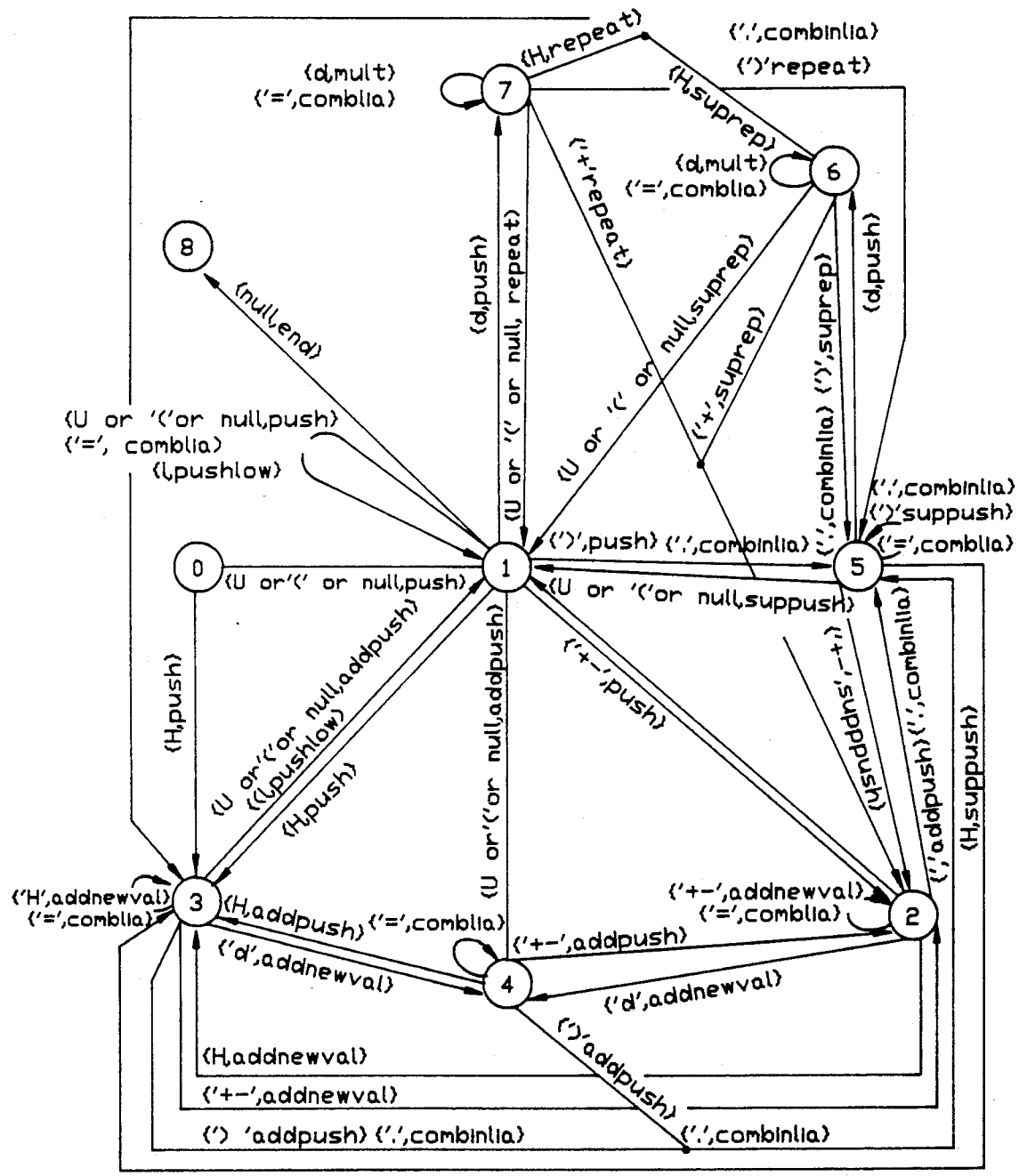
FIG. 14 is a diagrammatic representation of a state machine used to create a stack of substring atom representations.

The states generated during the Create-Stack routine are shown in Fig. 14.

ACTIONS 1. push - push character and its most likely valence on the stack.
2. combinlia - add inliaison information with another substring.
3. comblia - add outliaison information with another substring.
4. addpush - pull an element from the Stack, combine with the previous, and push the last character entered.
5. pushlow - combine c lowercase with the last element of the Stack, get the new valence.
6. addnewval - combine c with the last element of the stack.
7. suppush - delete () and push c.
8. repeat - pull last element of the Stack (a digit d), repeat the previous character (d-1) times, push c.
9. suprep - pull last element of the Stack (a digit d), delete (), duplicate the contents between the parentheses (d-1) times, push the last character entered.
10. mult - in case of a digit combine the tens and units digit to create a correct numeric value

CONNECT

Pseudocode for creating the connectivity in chemical string parsing

Key to Symbols Used:
i, j, m, n = atoms
Same (i) = set of atoms that are the same as atom i
CL(m,n) = the connectivity table, atom m and n are connected with a valence bond of CL(m,n)
WVAL(i) = valence of atom i found in the stack information
Str(i) = structural data of atom i (determined in
 find-group) related to group definition found in the
 stack information. Type of information: beginning,
end of a group, single, double bond with the next "C" in the chain.

PARTIAL = has 5 different values
- -NO: No inliaison
- -SS: Substring, only one inliaison with the first atom.
- -LS: Elementary substring on the left side of the string, only one inliaison with the first or the last atom.
- -RS: Elementary substring on the right side of the string, only one inliaison with the first atom.
- -MS: Elementary substring in the middle of the string, one or two inliaison with the first or first and and last atom.

Assumptions of the Algorithm:
1. Atoms are fully bounded.
2. An atom is usually bounded to its neighbors.

Algorithm:

If PARTIAL introduce one inliaison to the first atom of valence > 1
call FIND_GROUP (see pseudocode below)
call CONNECT_BOND (see pseudocode below)

BEGIN
    call TEST (see pseudocode below)
    depending on the result (fully connected, continuity of the molecule) either exit or call a recovery process
      and repeat the test
    select
    when okay (OK) EXIT
    when needs - fg call FIND_GROUP (see New Valence)
    when needs - cb call CONNECT_BOND (see Othersol)
      go to BEGIN
(see for each recovery process the application conditions in the ALGORITHM)

CONNECT_BOND

```
For all atoms i
    if WVAL(i) <= 0 return i
end for

For all atoms i
    if WVAL(i) = 1 and WVAL(i-1) > number of Same(i)
        for all atoms j in Same(i)
            CL(i-1)(j) = 1
            WVAL(j) = 0
        end for WVAL(i-1) = WVAL(i-1) - Same(i)

end for

For all atoms i
    if not (Str(i) = NULL)
        connect it following this structure information
end for LOOP
For all atoms i
    if WVAL(i) > 0

START
    Find atom j with j > i and WVAL(j) > 0
        if WVAL(i) > WVAL(j)
            CL(i)(j) = WVAL(j)
            WVAL(j) = 0
            WVAL(i) = WVAL(i) - WVAL(j)
            go to START
        end if if WVAL(i) = WVAL(j)

if for all atoms p > j, WVAL(p) = 0
                CL(i)(j) = WVAL(j)
                WVAL(j) = 0
```

```
        WVAL(i) = 0
      go to LOOP else
        CL(i)(j) = WVAL(j) - 1
        WVAL(j) = 1
        WVAL(i) = 1
        go to START
      end if if WVAL(i) < WVAL(j)
        CL(i)(j) = WVAL(i)
        WVAL(j) = WVAL(j) = WVAL(i)
        WVAL(i) = 0
        go to LOOP
      end if end for end connect bond
```

FIND-GROUP

Pseudocode to find the groups during chemical string parsing

Key to Symbols Used:
FC = first C atom of the group
LC = last C atom of the group
nh = number of H in the group
ni = number of liaisons to the group
nvb = number of atoms of valence 1 before FC (maximum allowed 3)
no = number of O in the group
noh = number of H attached to the last O in the group
nn = number of N in the group
nnh = number of H attached to the first N in the group
ns = number of S in the group
nsh = number of H attached to the last S in the group
nva = number of atoms of valence 1 after LC SAME(i) = number of atoms of type i in nva, i is an atom
group_information = group information gotten by separate
       and saved in GSTACK Starting Conditions of the Algorithm:
1.  The group information refers to the first group in the
string that is not between parentheses
2.  Only the atoms connected to the first C may be written
before the carbons.
Algorithm:
if the string is an elementary substring push null to GSTACK
TOP
go through the stack and find a group with N or S
   if N go to NITRO_GROUP
   if S go to SULFUR_GROUP
START
go through the stack and find a group with C
if not found
       pop one element of GSTACK
       if this element is not null flag an error (unused
         front information)
       end of FindGroup
else if found
       get the information FC,LC,nvb,nva,ni,SAME(i)
       nh = 4 - val(LC)
       if nc = 6 go to BENZENE_RING
       if nc = 2 go to ETHYL_GROUP
       else
       LINEAR_GROUP
       if information on GSTACK is related to linear group
          pop all group_information from GSTACK
          push NULL information
       else group_information = NULL
       depending on the group_information, nh, ni, SAME(i)
             and nc
          adjust nvb and nva
          attach the H to the C, (filing up the C in a
             sequential order)

```
   interleave the other atoms between the C
   end LINEAR_GROUP
   go to START BENZENE_RING
if nh > 6 goto LINEAR_GROUP
if nh = 6 and nothing else is on the stack
   attach one H to each C
   add Double and Single bond information
   go to end BENZENE_RING
else go to LINEAR_GROUP
if nh = 5
   attach one H to each C (with a maximum of 5 H)
   add Double and Single bond information
   go to end PHENOL_RING if SAME(i) > 6 and nh = 0 go to LINEAR_GROUP
if nh = 0 and SAME(i) = 6
   if something else is on the stack then go to
       LINEAR_GROUP
   else
   interleave one atom after each C
   add Double and Single bond information
   got to end PHENOL_RING
if nh < 2 and SAME(i) = 5
   interleave one atom after each C (with a maximum of
       5 atoms)
   add Double and Single bond information
   go to end PHENOL_RING
else
   if information on GSTACK is related to phenol group
   pop all group_information from GSTACK
   push NULL information
else group_information = NULL
depending on the group_information, nh, ni, SAME(i)
       and nc
   adjust nvb and nva (maximum for nvb = 1)
   attach the H to the C, (filing up the C in a
``` sequential order)
    interleave the other atoms between the C
    add Double and Single bond information
end PHENOL_RING
go to START ETHYL_GROUP
if nh = 4
    if group does not use all stack go to LINEAR_GROUP
    else
    attach two H per C
    add Double bond information
if nh + nva + ni + nvb > 4 (maxi nvb = 2) go to
    LINEAR_GROUP
if nh + nva + ni + nvb = 4 (maxi nvb = 2)
    if something else is on the stack then go to
LINEAR_GROUP if nh = 2
    if information on GSTACK is related to ethyl group
        pop all group_information from GSTACK
        push NULL information
    else ambiguous = TRUE
        attach one H to each C
        interleave the other atoms inbetween the C
        add Double bond information
        go to end ETHYL_GROUP
if same(i) = 2
    if information on GSTACK is related to ethyl group
        pop all group_information from GSTACK
        push NULL information
    else ambiguous = TRUE
        interleave one i atom between the C
        interleave the other atoms between the C
        add Double bond information
        go to end ETHYL_GROUP
else
    interleave the nvb atoms related to the first C

```
        attach the H to the C, (filing up on the C in a
          sequential order)
        interleave the other atoms between the C
        add Double bond information
end ETHYL_GROUP
go to START NITRO_GROUP
get the information nn, nnh, no, noh.
if nn = 1
    if no = 2 and nnh <2 and noh = 0
        add double and single bond information between
            N and O's
        add +valence to N
        add -valence to one O
    if no = 2 and nnh = 0 and noh = 1
        no = 1
        noh = 0
            attach the H to the second O
    if no = 1 and nnh < 2 and noh = 0
        add double bond information between N and O end if nn = 1
if nn = 2 and nnh < 3
    add double bond information between N's
end if nn = 2 if nn = 3 and nnh < 2
    add double bond information between N's
    add +valence to the second N
    add -valence to the last N
end if nn = 3 end NITRO_GROUP
go to TOP

SULFUR_GROUP
get the information ns, nsh, no, noh.
```

```
if no = 0
     valence of S's is 2
end if no = 0 if ns < 1
     valence of S's is 2 except for the last one
     ns = 1
     new value of nsh (related to the last one)

if no = 1
     valence of S is 4
     add double bond information between S and O
end if no = 1 if no = 2 and ((noh < 3 and nsh = 0) or (noh = 0 and
     nsh < 3))
     valence of S is 6
     add double bond information between S and O's
     attach the H's to the S
end if no = 2 if no = 3
     valence of S is 6
     add double bond information between S and two O's
     add single bond information between S and the
        reminding O
     if noh + nsh = 2
        attach H to the single bonded O
        attach H to the S
     else
        if noh = 1 attach H to the single bonded O
        if nsh = 1 attach H to S
end if no = 3 if no = 4
     valence of S is 6
     add double bond information between S and two O's
``` add single bond information between S and the
            reminding O's
        attached the H to the single bonded O's
    end if no = 4
end SULFUR_GROUP go to TOP TEST
Pseudocode for testing the connectivity in chemical string parsing.

Key to Symbols Used:
i, j, m, n = atoms
WVAL(i) = valence of atom i after connectivity table formed.
CL{m,n} = the connectivity table, atoms m and n are
    connected with a valence bond of CL{m,n}
TCON = set of atoms connected together
CON = number of atoms in TCON
FULLCONNECT = memorize the first atom number not fully
    connected
DISCONNECT = memorize the first atom number of the
    molecular discontinuity Assumptions of the Algorithm:
1.  All atoms must be fully connected.
2.  All atoms must be in one molecule or set.

Algorithm:
FULLCONNECT = any
DISCONNECT = any for all atoms i
    if WVAL(i) not null
    FULLCONNECT = i and exit the loop
end for create an empty set TCON Add the first atom in the set
   Add its Children (see pseudocode below)
DISCONNECT = first atom not in TCON
   end Test Add Children of atom j
for i (in a column)
      if CL(i,j) is connected
         if i is not in TCON
            add i
            CON = CON + 1
            Add Children of i
         end if
      end if
end for
If CON = Maximum (all atoms are in the set) EXIT
else
for i (in a line)
      if CL(j,i) is connected
         if i is not in TCON
            add i
            CON = CON +1
            Add Children of i
         end if
      end if
end for
end Add Children of j

NEW VALENCE

Pseudocode for newvalence in chemical string parsing

Key to Symbols Used:
i, j = atoms
FVAL(i) = full valence of atom i in valence table
      used to determine VAL(i)
new_VAL(i) = valence of atom i in valence table not used
VAL(i) = valence of atom i in the stack
dif = difference between new and old valence PB(i) = probability related to a valence (in the valence table)

MAXI_PROBABILITY allowed

SAME(i) = number of atoms identical to i

Starting Conditions of the Algorithm:
1. Atoms have no more than two main valences
2. Only a few atoms in a string have two valences
3. Atoms A written in the form Ad, have the same valence Algorithm:
    Process 1

1. Process 1 is used when atom i is not fully connected, and before the Recover process.
2. The process tries to find a smaller valence for i, or an atom j before i with a new valence higher than used in the first treatment. If the valence of an atom is changed, the program returns to Find Group using the new resultant stack as input (see Connect).

```
if PB (i) > MAXI_PROBABILITY
   go to BEFORE
       dif = new_VAL(i) - FVAL(i)
       find SAME (i)
       if (SAME(i) = 1 and -dif = WVAL(i) or
           (SAME(i) > 1 and -dif*SAME(i) > WVAL(i))
         replace FVAL(i) by new_VAL(i) for all atoms i
         go to CONNECT
BEFORE
       find atom j before i with lowest PB(j) and
           (dif = new_VAL(i) - FVAL(i)) > 0
       find SAME (j)
       if dif*SAME(j) > = WVAL(i)
         replace FVAL(j) by new_VAL(j) for all atoms j
         go to CONNECT
go to RECOVER
end process 1
```

Process 2

1. Process 2 is used if more than one molecule and after the Recover process 4 in the first molecule, find the atom with the lowest probability, and replace its valence. The program is returned to Find Group using the new resultant stack as input.

```
    find atom j before i with lowest PB(j)
       if PB(j) < MAXI_PROBABILITY
           find SAME(j)
           replace FVAL(j) by new_VAL(j) for all atoms j
           go to Find Group
end process 2
```

OTHERSOL

Pseudocode to find other solution in case of errors in the connectivity table when the string ended with a sign in chemical string parsing Key to Symbols Used:
i = atoms
BL(m,n), CL(m,n) = the connectivity tables, atoms m and n
    are connected
VAL(i) = valence of atom i, information given in the stack
WVAL(i) = valence of atom i, used during the connection
FIRSTSOL = indicate multiple solutions Assumptions of the Algorithm:
1. If a string is of the form SAdSs (N(CH3)2-) the atoms A have identical roles, the ending sign cannot report to them.

Algorithm:

1. Used when a molecule has an ending sign and no solution is found when reporting the sign to the last atom of the string.
2. The process goes through the string to find the atom that can support the sign. If more than one solution the ambiguity is mentioned to the user.

```
FIRSTSOL = FALSE
START
For all atoms i
    WVAL{i} = VAL{i}
end for

For all atoms i
    If atom can receive the endsign and WVAL{i} - endsign > 0
        WVAL{i} = WVAL{i} - endsign
        BL{}{} = connectivity table of the molecule in
            using WVAL{i} (Connectivity table generated by
            inputing new resultant stack to Connect Bond
            procedure)
        if BL{}{} is a solution
            if FIRSTSOL = FALSE
                FIRSTSOL = TRUE
                copy BL{}{} in CL{}{}
            else interact with the user
            end if
        go back to START
        end if
end For
end Othersol
```

RECOVER

Pseudocode to recover the errors in the connectivity table in chemical string parsing.

Key to Symbols Used:
i, j, m, n, lastA, num = atoms
first = an atom having an inliaison
last = last atom of valence > 1 that is not fully connected
firstC, lastC = an atom of Carbon
INLIAISON{i} = value of the inliaison of atom i
CL{m,n} = the connectivity table, atom m and n are connected
    with a valence bond of CL{m,n}
DIV, a, b = a valence Assumptions of the Algorithm:

1. an elementary substring between parentheses is an entity on its own, with one or two atoms (first or the last) connected to the rest of the substring.

2. The connectivity between an elementary substring and the whole substring is of valence one or two.

3. An atom must be connected to another one that is as close as possible to it in the string description.

Algorithm:

Process 1

1. Process 1 is used
   when there is an elementary substring between parentheses followed by a digit
   when the last atom has a valence > 1, is not fully connected, a value of 1 is leftover, and the molecule is not cut.

2. The process adds an inliaison to the last atom that is not fully connected.

INLIAISON(last) = 1

End process 1

Process 2

1. Process 2 is used
   when there is an elementary substring between parentheses at the beginning of the string,
   when the last atom has a valence > 1, is not fully connected, a value of 2 is left over, and the molecule is not cut.

2. The process adds an inliaison to the last atom in the string, deletes the inliaison from the first atom, and adds a conection between the first and the last.

INLIAISON(first) = 0
   INLIAISON(last) = 1
   CL(first, last) = 1 end process 2

Process 3

1. Process 3 is used when one atom is not fully connected, an even number of valences are left over, and the molecule is cut just before i.

2. The process cuts the bond between the two previous atoms and connects them to the not fully connected atom to form a triangular bond.

DIV = Valence that needs to be cut.

Find the two atom i, j just before m that are connected

```
if CL{i,j}> = DIV
    CL{i,j}  = CL{i,j} - DIV
    CL{i,m}  = DIV
    CL{j,m}  = DIV
end if
```
If not found return error
End process 3

Process 4

1. Process 4 is used when there are more than one molecule (but not fully conencted).

2. In the second molecule the process finds the first carbon (firstC) and the last atom (lastA) in the string connected to it. Then the process finds between firstC and lastA a carbon that is connected to firstC, (lastC).

3. The process disconnects firstC and lastA, firstC and lastC; and connects lastC and last.

4. FirstC is not fully connected, use Recover process 3 to add an inliaison bond with the first molecule.

```
For i > num (last atom of the first molecule)
    find firstC
end for
For i > firstC
    find lastA, atom connected to firstC
    b = CL{firstC, lastA}
end for
For firstC < i < lastA
    find lastC
```

```
        a = CL(firstC, lastC)
        if a >= b
            CL(firstC, lastC) = a - b
            CL(lastC, lastA) = b
            CL(firstC, lastA) = 0
            Call process 1 with firstC
        end if
end for
end process 4
```

DRAW A MOLECULE

Pseudocode to define the position of all atoms of a connectivity table in chemical string parsing.

Key to Symbols Used:

a = atom
fa = first atom of a list, la = last atom of a list
Str(m) = structural data of atom m
useful values Bz = Benzene ring, TB = Triangular Bond,
LL = list, ET = ethyl group
MASK(m) = an atom has 8 directions available for its connections, MASK is formed by 8 bits, each one representing one direction, a used direction change its bit from 0 to 1
FROM(m) = atom used to determine the position for atom m
POS(m) = (x, y, bl) position of atom m and its bond length
DR(m) = direction used to position atom m
possible direction: 0 for East, 1 for North-East, 2 for North, 3 for North-West, 4 for West, 5 for South-West, 6 for South, 7 for South-East
CHID(m) = direction choice used to position atom m
ALLATOM(p) = list of all atoms classified in decreasing order by their number of connections
PROCESSLIST(i) = list of atoms in their processed order used to backtrack.

Assumptions of the Algorithm

1. The only loops possible are triangular bonds and Benzene rings.

Algorithm

For each atom determine the number of atoms connected to it in ALLATOM and classify them in a decreasing order following these values
p = 0

For each atom initialize its CHID to -1, its MASK to 0

Transfer the BZ and ET structure information of an atom existing in a previous table where it was involved in such structure.
Find all Clist (see pseudocode in FIND STRUCTURES), classify them by length, delete all unusable lists
The lists ending with a Benzene ring are inverted
For all atoms or elements of a list
  if Str(a) <> BZ
  Str(a) = LL Find all triangular bonds
(see pseudocode in FIND STRUCTURES)

Take the longest list starting and ending with a Benzene ring
if none take longest starting with a Benzene ring
if none take the longest list and go to NOLISTRING DR(fa) = 0
POS(fa) = (0, 0, bl)
CHID(fa) = 0
FROM(fa) = -1
i = 1
PROCESSLIST(i) = fa
DrawRing(fa) (see pseudocode in FindNext Position
    procedure)

DR(fa) = 4
DrawList(fa) (see pseudocode in FindNext Position
    procedure)
If list end with a Benzene ring, DrawRing(la)

BENZENERING
    find list not drawn starting or ending with a Benzene
        ring drawn
        (if ending inverse the list)
        if none go to LISTBEGIN
        DrawList(fa)
        If list end with a Benzene ring, DrawRing(la)
        go to BENZENERING NOLISTRING
    DR(fa) = 4
    POS(fa) = (0, 0, bl)
    CHID(fa) = 0
    FROM(fa) = -1
    PROCESSLIST(0) = fa
    i = 1
    DrawList(fa)
    DR(fa) = 0

LISTBEGIN
    find list not drawn having first or last atom drawn
    (if last inverse the list)
    if none go to NEIGHBOR
    DrawList(fa)
    If list end with a Benzene ring drawring(la)
        go to BENZENERING
    else go to LISTBEGIN NEIGHBOR
    If ALLATOM(p) is not drawn swap with the next until
    find one that is drawn
    If none go to NEW
    DrawNeighbor(ALLATOM(p))
    (see pseudocode in FindNext Position procedure)

```
    if Str(PROCESSLIST(i)) = BZ (last atom drawn)
        DrawRing (PROCESSLIST(i))
        go to BENZENERING if Str(PROCESSLIST(i) = LL (last atom drawn)
        cut the list into two lists at PROCESSLIST(i)
        DrawList (PROCESSLIST(i))
        if Str(PROCESSLIST(i)) = BZ (last atom drawn)
          DrawRing (PROCESSLIST(i))
        DrawList (PROCESSLIST(i))
        if Str (PROCESSLIST(i)) = BZ (last atom drawn)
          DrawRing (PROCESSLIST(i))
        If a ring was drawn go to BENZENERING else, go to LISTBEGIN else p = p + 1
    if all atoms were considered end of drawnmolecule
    go to NEIGHBOR NEW
fa = ALLATOM(1)
DR(fa) = 0
POS(fa) = (0, 0, bl)
CHID(fa) = 0
FROM(fa) = -1
i = 1

PROCESSLIST(0) = fa
    if Str(fa) = BZ
    DrawRing(fa)
    (see pseudocode in FindNext)
  else
    DrawNeighbor(fa)
    p = p + 1
    if all atoms were considered end of Draw Molecule
    DR(fa) = 4
  Go to NEIGHBOR
```

FIND STRUCTURES

Pseudocode to find structural information to drawn the connectivity table in chemical string parsing.

Key to Symbols Used:

a, b, c, d, = atoms
Str(m) = structural data of atom m
usefull values Bz = Benzene ring, TB = Triangular Bond,
LL = List, ET = Ethyl group
NLIAISON(a) = number of atoms connected to a
CL(m,n) = the connectivity table, atom m and n are connected with a valence bond of CL(m, n)
PATH(i) = one list of carbons, indexed by i
LIST(n) = lists of carbons, indexed by n
NEW = flag that indicate if some atoms where found or where to start the new research for the path Assumptions of the Algorithm
1. the connection table is simple, the only loop possible are triangular bonds or Benzene rings Algorithm

- Find Triangular Bonds (Find TB)

```
For all atoms having a NLIAISON(a) > 1
    find atom b and c such that
        CL(a,b) > 0
        CL(a,c) > 0
    if CL(b,c) > 0
        Str(a) = TB
        Str(b) = TB
        Str(c) = TB
    end if
    end find
end for
```

End Find Triangular Bonds

- Find Clist (list of carbons in the connectivity table)
- Find Clist is a deep first search algorithm to find all paths on a tree, adapted to a connectivity table. (Mulitiple roots, bidirectional branches, only loops possible are formed by three atoms or Benzene ring that are marked.)

```
n = 0
BEGIN
For all atoms a such that name(a) = 'C' and
      Str(a) is not Ethyl and a is not marked
      NEW = -1, i = 1
      PATH(0) = a
LOOP
      find atom b, such that name(b) = 'C' and
        b > NEW and Str(b) is not Ethyl and
        if i > 1 b different from PATH (i - 2)

PATH(i) = b, i = i + 1
          if Str(b) = BZ
            if Str(a) = BZ go to BEGIN
            else go to BZEND
          else a = b, NEW = 0, go to LOOP
      BZEND
        else (b not found)
            if NEW <> 0 (no new list found) mark PATH (i-1)
              if i < 2 go to BEGIN
            if NEW = 0 copy PATH in LIST(n), n = n + 1
            i = i - 1
            NEW = PATH(i)
            a = PATH (i-1)
            go to LOOP
end Find Clist
```

Find ET

FIND NEXT POSITION

Pseudocode to find next position available to draw the connectivity table in chemical string parsing Key to Symbols Used:

a, b, c, d, = atoms
Str(m) = structural data of atom m
usefull values Bz = Benzene ring, TB = Triangular Bond, LL = List, ET = Ethyl group
CL(m,n) = the connectivity table, atom m and n are connected with a valence bond of CL(m,n)
TABLE(m) = connectivity table pointed by m, it is not null if m is an atom of an elementary substring include in the one proceed
MASK(m) = an atom has 8 directions available for its connections, MASK is formed by 8 bits, each one representing one direction, a used direction change its bit from 0 to 1.
FROM(m) = atom used to determine the position for atom m
POS(m) = (x, y, bl) position of atom m and its bond length
POS1 = an atom position
DR(m) = direction used to position atom m
possible directions: 0 for East, 1 for North-East, 2 for North, 3 for North-West, 4 for West, 5 for South-West, 6 for South, 7 for South-East
DR1, DR2 = direction
CHID(m) = direction choice used to position atom m
CHOICE = direction choice
R(DR) = translation matrix following the DR direction
MDR(DR) = mask corresponding at DR direction (all bit at 1 except for DR bit)
INV(MDR(DR)) = function that inverse the direction mask
OR, AND logic operator on mark
FULLMASK = mark of all 1
POS2 = MULT (R1, POS1) operation that multiply a rotatino translation matrix with a position matrix to produce a new position.

NEXT{CHOICE} = value to add at a direction to find a new direction
L1, L2, LIST = lists of carbons
FA = first atom of a list
LA = last atom of a list
IA = an atom of a list
RANK = rank of the Carbon atom in a Benzene ring
PROCESSLIST{i} = list of atoms in their processed order used to backtrack and to recover a conflict
S flag used in insert table Assumptions of the Algorithm 1. No atom can have more than 8 connections.
2. Atoms are preferably attached in opposite directions, if not possible perpendicularly to each other, the last solution would be with a 45 degree angle.
3. Consider a grid, atoms can be placed only at intersections of the horizontal and vertical grid lines. Therefore, diagonal bond lengths are longer than horizontal and vertical bond lengths.

Algorithm

```
- DrawList(c)
    draw a list starting with c (c is drawn)
a = c, j = 1
BEGIN
  if TABLE (a) = TABLE (a + 1) and not null
      Insert (TABLE(a)) (case of repeating parentheses)
      (see pseudocode below for INSERT TABLE)
      if a + 1 is the next atom in the list, a = a + 1
b next atom in the list after a
If Str(a) = TB and Str(b) = TB
      DrawTB (a, b) (see pseudocode below for DrawTB)
      go to BEGIN
  if FindNext (a, b) = error (see pseudocode below for
      FindNext)
      clear j atoms
      go to BEGIN
```

```
PROCESSLIST(i) = b
i = i + 1  j = j + 1
a = b
if a is last of the list
     (case of pendant parentheses or digit front
     information) insert all TABLE (PROCESSLIST(i)) not
     previously inserted
     End of DrawList
go to BEGIN

- DrawNeighbor(a)
     draw all not drawn atoms connected to a (a drawn)
j = 1
BEGIN
     if TABLE(a) not null Insert (TABLE(a))
     find b not drawn atom connected to a
     If no b end DrawNeighbor
     If Str(b) = BZ
          if FindNext (a, b) = error go to BACKTRACK
          end DrawNeighbor
     If Str(b) = LL
          if FindNext (a, b) = error got to BACKTRACK
          end DrawNeighbor
     If Str(a) = TB and Str(b) = TB
          if DrawTB (a, b) = error go to BACKTRACK
          j = j + 2
     If Str(b) = ET
          if DrawET (a, b) = error go to BACKTRACK
          (see pseudocode below for DrawET)
          j = j + 5
     else
          if FindNext (a, b) = error go to BACKTRACK
          PROCESSLIST (i) = b
          i = i + 1, j = j + 1
     go to BEGIN
BACKTRACK
     If Str(a) = NULL and Table (a) = NULL
          clear j atoms from PROCESSLIST
```

```
            (new position for a)
            if FindNext (FROM(a), a) = error
            if ResolveConflict (a, b) = error see user
            go to BEGIN
        else if resolve conflict (a, b) = error see user
            go to BEGIN ResolveConflict (a, b)
    find a possible position for b where b conflicts with c
    c not connected to a, c after a in AllAtom,
    Str(c) = NULL and Table (c) = NULL
        (new position for c)
        if FindNext (FROM(c), c) = error
        if ResolveConflict (FROM(c), c) = error return
           error
        give b the previous coordinates

- FindNext (a, b)
        find position of atom b next to atom a
        successive values of NEXT(CHOICE)
        (4,6,2,5,1,3,7,0)

If (DR(a)) modulo 2 = 0
        DR1 = DR(a)
else
        DR1 = (DR(a) + 1) modulo 8
end if
CHOICE = CHID(b)
BEGIN
    CHOICE = CHOICE + 1, if CHOICE > 7 error
    DR2 = (DR1 + NEXT(CHOICE)) modulo 8
    If MASK(a) OR MDR(DR2) = FULLMASK go to BEGIN POS1 = MULT (R(DR2), POS(a))
    If find atom c at POS1 go to BEGIN POS(b) = POS1
    MASK(a) = MASK(a) OR INV(MDR(DR2))
```

```
    DR(b) = (DR2 + 4) modulo 8
    FROM(b) = a
    CHID(b) = CHOICE
    MASK(b) = MASK(b) OR INV (MDR(DR(b)))
end if End FindNext

- DrawRing (c)
        draw a Benzene ring starting at atom c (c is
        drawn)
If TABLE(c) not null
    Insert (TABLE(c))
    end DrawRing
d atom of the ring after c
BEGIN
    CHOICE = CHID(d) + 1, if CHOICE > 6 error
    a = c
    RANK = 0
LOOP
    b atom of the ring after a
    if FindNextRing (a, b, CHOICE, RANK) = error
    (see pseudocode below for FindNextRing)
        clear (RANK + 1) atoms from PROCESSLIST
        go to BEGIN
    PROCESSLIST(i) = b
    i = i + 1
    a = b
    RANK = RANK + 1
    if RANK = 7 End drawring
    go to LOOP

- FindNextRing (a, b, CHOICE, RANK)
        find position of atom b next to atom a in a
          Benzene ring
        NEXT depend on two items of information: CHOICE
and RANK of the Carbon atom in the ring
        successive values of NEXTRING(CHOICE, RANK)
```

```
0.  (3,5,5,6,5,6,6)
1.  (3,6,5,5,6,7,2)
2.  (2,5,6,5,5,7,2)
3.  (1,5,5,6,5,6,6)
4.  (5,5,5,6,5,6,6)
5.  (4,5,6,5,5,7,4)
6.  (1,6,5,5,6,7,2)

DR1 = (DR(a) + NEXTRING(CHOICE, RANK)) modulo 8
If MASK(a) OR MDR(DR1) = FULLMASK return error
If RANK = 0
    If CHOICE is 0 or 3 or 4
        If MASK(a) OR MDR (DR1 + 2) = FULLMASK return
            error
    else
        If MASK(a) OR MDR (DR1 + 3) FULLMASK return error
    POS1 = MULT(R(DR1), POS(a))
    If find atom c at POS1 return error
    POS(b) = POS 1
    MASK(a) = MASK(a) OR INV(MDR(DR1))
    DR(b) = (DR1 + 4) modulo 8
    FROM(b) = a
    CHID(b) = CHOICE
    MASK(b) = MASK(b) OR INV(MDR(DR(b)))
end FindNextRing drawTB(a,b)
    draw a triangular bond existing between atoms a,b and
    c.  Atom a is drawn.
    A fictitious atom f is added to avoid any atom to use
    the middle point of a b.

find atom c connected to atoms a and b.
    initialize a fictitious atom f.

BEGIN if FindNext(a,f) = error return error
```

(undo the MASK(a), to allow b to use the same direction)

MASK(a) = MASK(a) AND
    MDR((DR(f) + 4) modulo 8)
change in POS(a) the bond length to 2*bl
CHID(b) = CHID(f) - 1 if FindNext(a,b) = error return error if not (DR(b) = DR(f))
    CHID(f) = CHID(b) - 1
    change in POS(a) the bond length back to bl
    clear 2 atoms from PROCESSLIST
    go to BEGIN change in POS(a) the bond length back to bl LOOP
    if CHID(c) > 1
        CHID(c) = -1
        clear 2 atoms from PROCESSLIST
        go to BEGING DR1 = DR(a) + (NEXT(CHID(b)) + CHID(c) + 8) modulo 8
    If MASK(a) OR MDR(DR1) = FULLMASK
        CHID(c) = CHID(c) + 2
        go to LOOP POS1 = MULT(R(DR1), POS(a))
    If find atom c at POS1
        CHID(c) = CHID(c) + 2
        go to LOOP POS(c) = POS1
    DR2 = (DR1 + 2*CHID(c) + 8) modulo 8
    MASK(a) = MASK(a) OR INV (MDR(DR1))
    MASK(b) - MASK(b) OR INV (MDR(DR2))

FROM(c) = a
    DR(c) = (DR1 + 4) modulo 8

```
        DR2 = (DR2 + 4) modulo 8
        MASK(c) = MASK(c)
              OR INV(MDR(DR(c)))
              OR INV(MDR(DR2))
              OR INV(MDR(DR2 + DR(c))/2))
        PROCESSLIST(i) = c
        i = i + 1 end DrawTB

DrawET(a,b)
        Draw an ethyl group, a is drawn, b is a carbon atom of
        the group, and Str(b) = b
        If a Carbon atom of Structure ET has an inliaison, this
        inliaisoin is replaced by a fictitious atom f.
if TABLE(b) is not NULL
        insert (TABLE(b))
        where atom a will correspond to the fictitious atom
        connect to b
        in TABLE(b)
        end DrawEt if Str(a) = CIS TYPE = CIS
if Str(a) = TRANS TYPE = TRANS
else TYPE = NULL
ORDER = 0
CHOICE = CHID(b)

BEGIN
      CHOICE = CHOICE + 1
if CHOICE > 9 return error
j = 0
if FindET (a,b,CHOICE,0) = error go to BACKTRACK
j = 1 find Carbon atom c not drawn, connected to b and Str(c)
= ET
if FindET(b,c,CHOICE,1) = error go to BACKTRACK
j = 2
```

```
find atom d not drawn, connected to b
if not found and inliaison of b > 0
    decrement the inliaison of b
    initialize a fictitious atom f connected to b
    d = f if Str(a) = CIS TYPE = CIS, ORDER = 1
if Str(a) = TRANS TYPE = TRANS, ORDER = 1 if FindET(b,d,CHOICE,2) = error go to BACKTRACK
j = 3 if TYPE not NULL
    find atom e not drawn, connected to c and Str(e) =
    TYPE
    if not found and inliaison of c > 0
      decrement the inliaison of c
      initialize a fictitious atom f connected to c
      e = f
    if TYPE = TRANS
      if FindET(c,e,CHOICE,3 + ORDER) = error go to
      BACKTRACK
      RANK = 4 - ORDER
      j = 4 if TYPE = NULL
    find atom e not drawn, connected to c
    if not found and inliaison of c > 0
      decrement the inliaison of c
      initialize a fictitious atom f connected to c
      e = f if findET(c,e,CHOICE,3) = error go to BACKTRACK
      RANK = 4
      j = 4 find atom g not drawn, connected to c
if not found and inliaison of c > 0
``` decrement the inliaison of c initalize a fictitious atom f connected to c g = f if FindET(c,g,CHOICE,RANK) = error go to BACKTRACK end DrawET

BACKTRACK clear j atoms from PROCESSLIST go to BEGIN

FindET(a,b,CHOICE,RANK)

find position of atom b next to atom a in an Ethyl group

NEXTET depend on two informations: CHOICE and RANK of the Carbon atom in the group successive values of NEXTET(CHOICE,RANK)

0. (5,3,6,3,5)
1. (5,5,2,5,3)
2. (3,5,2,5,3)
3. (3,3,6,3,5)
4. (6,3,6,3,5)
5. (6,5,2,5,3)
6. (2,5,2,5,3)
7. (2,3,6,3,5)
8. (4,5,2,5,3)
9. (4,3,6,3,5)

DRI = (DR(a) + NEXTET(CHOICE,RANK)) modulo 8

If MASK(a) OR MDR(DR1) = FULLMASK return error

POS1 = MULT(RDR1), POS(a))

If find atom c at POS1 return error

POS(b) = POS1

MASK(a) = MASK(a) OR INV(MDR)DR1))

DR(b) = (DR1 + 4) modulo 8

FROM(b) = a

CHID(b) = CHOICE

MASK(b) = MASK(b) OR INV (MDR(DR(b)))

end FindET

- Insert (TABLE)

insert a connectivity table that was created and
    drawn previously the table is connected through atom a.  All
    the values in the previous table will be pre-
    ceeded by "Old"

BEGIN

For all atoms in TABLE do

Translation (POS(a) - OldPOS(a))

S = 0

LOOP

If find no conflicted atom go to END

For all atoms in TABLE do

Symmetry (axe X = x component of POS(a))

If find no conflicted atom go to END

For all atoms in TABLE do

Symmetry (axe Y = y component of POS(a))

If find no conflicted atom go to END

For all atoms in TABLE do

Symmetry (axe X = x component of POS(a))

If find no conflicted atom go to END

For all atoms in TABLE do if S = 0, Rotation (90 degree), S = 90, go to LOOP if s = 90, Rotation (45 degree), S = 45, go to LOOP if S = 45 if findnext (FROM(a),a) = error see user go to BEGIN

END

MASK(a) = MASK(a) OR OldMASK(a)

APPENDIX K
AGGREGATION

Pseudocode for creating the molecular structure file for a diagram from a scanned image.

KEY TO SYMBOLS USED:

A = atom (V vertex, M meaning)
AL = set of atoms
TCON = stack FIFO of atoms
TOP, BOTTOM = indices to TCON stack

STARTING CONDITIONS OF THE ALGORITHM.

1. Each atom in a molecule must have at least one connection (bond). If an atom has no connection, it is not part of the molecule.

2. A molfile is composed of two tables:
   a. table of atoms with their coordinates
   b. table of bond connectivity referring to the previous atom table
3. There is only one molecule, all atoms are connected together.

ALGORITHM.
Count the number of connections in the structure by going through AL.

Create an empty Molecular Structure File

```
For all atoms A in AL
   if A is a connection
   add it to the atom table with its coordinates
   memorize in A status its position in the table
else A status = NO ATOM
End For
```

```
TOP = BOTTOM = 0
TCON(TOP) = first atom in AL
REPEAT
      A = TCON(BOTTOM)
      A status = TREATED
      BOTTOM = BOTTOM + 1 for all connection V to A
         if V status is atom and not TREATED
            count number of connections between A and V
            add this connection to the connectivity table
            TOP = TOP + 1
            TCON(TOP) = V
      end for all V if BOTTOM <= TOP go to REPEAT For all atoms A in AL
      if A status is atom not TREATED flag the error end of aggregate
```

APPENDIX L
POST PROCESS
MEMORY CLEANUP

Pseudocode for memory cleanup for a diagram from a scanned image.

KEY TO SYMBOLS USED:

G = (gheight, gwidth, X, Y, Class, set of vertices in the group)
SG = set of group
GL = group letter (position = group, meaning)
ST = string set of groups letter
S = set of strings
A = atom (V vertex, M meaning)
AL = set of atoms

STARTING CONDITIONS OF THE ALGORITHM.

1. We have access to all memory space used.

ALGORITHM.

The following algorithm frees all the data stored in memory for the process.

```
For all group G in SG
   free all the vertices attach to it.
   free the group G free SG For all atom A in AL
   free the meaning
   free the atom A free AL For all string ST in S
   free the letter
   free ST free S end of memory cleanup
```

What is claimed is:

1. In a data processing system including a central processing unit (CPU), an optical scanner for generating a two-dimensional binary array representation of a textual input, and a memory, a system for optical recognition of chemical graphics, comprising:
   separation means for receiving a binary array of picture components representing a textual input which includes printed chemical structure indicia and for generating ana isolated array of picture components representing said chemical structure;
   vectorization means responsive to said isolated array of picture components for generating a vector representation of said printed chemical structure;
   segmentation means responsive to said vector representation for separating character information from graphics information in said vector representation into sets of connected character vectors and sets of connected graphics vectors;
   vector cleanup means responsive to said set sets of connected graphics vectors for eliminating redundant vectors and vector junctions to generate optimized sets of connected graphics vectors;
   optical character recognition means responsive to said sets of connected character vectors for generating character identification codes corresponding to said sets of connected character vectors;

graphical structure recognition means responsive to said optimized sets of graphics vectors for constructing an array of atoms and associated bond structure;

chemical formula recognition means for automatically identifying chemical substrates in response to said character identification codes and generating chemical substructure connection tables; and aggregation means for combining said chemical substructure connection tables with said array of atoms to generate a complete molecular structure file listing of atoms and associated bond structure.

2. The data processing system of claim 1 wherein said separation means includes means for identifying groups of connected picture components for representing chemical structure and associated character strings and separating said groups of connected picture components from picture components that do not represent chemical structures.

3. The data processing system of claim 2 wherein said vectorization means are responsive to said groups of connected picture components for generating vector representations of connected picture components in said groups of connected picture components.

4. The data processing system of claim 1 wherein said segmentation means includes means for constructing groups of connected vectors, and for classifying said vector groups into chemical bonds, circles and characters.

5. The data processing system of claim 4 wherein said segmentation means includes means for identifying strings of adjacent connected vector groups classified as characters and coordinate positions of the characters.

6. The data processing system of claim 1 wherein said vector cleanup means includes means for detecting vectors having a length less than a predetermined fraction of a longest vector, for deleting such vectors, and for reconnecting vectors previously connected to the removed vector to the previous midpoint of the removed vector.

7. The data processing system of claim 1 wherein said vector cleanup means includes means for detecting and removing redundant vectors at pints remote from the vector junctions by measuring an angle of intersection at vertices where exactly two vectors meet and, if the angle is less than a predefined value, removing the vortex.

8. The data processing system of claim 1 wherein said graphical structure recognition means includes means for identifying carbon atoms in said array of atoms at node locations where two bonds meet and reserving other node locations for chemical substructures identified by said chemical formula recognition means.

9. The data processing system of claim 4 wherein said graphical structure recognition means includes means for converting circular connected vector groups into a series of double bonds.

10. The data processing system of claim 1 wherein said optical character recognition means extracts from the position of a character in the image a normalized binary array for each character to have the maximum information for the recognition.

11. The data processing system of claim 1 wherein said optical character recognition means includes means for displaying connected character strings for manual identification.

12. A method executable on a digital computer for optically recognizing and generating a molecular file representation of chemical graphics, comprising the steps of:

scanning an input of printed text having a chemical structure printed thereon, and generating a two-dimensional binary array of picture components representing said text;

generating an array subset of said binary array of picture components corresponding to said chemical structure;

vectorizing said array subset to generate a vector representation of said chemical structure from said array subset;

segmenting said vector representation into sets of connected character vectors and sets of connected graphics vectors;

eliminating redundant vectors and vector junctions and generating optimized sets of connected graphics vectors from said sets of connected graphics vectors from said sets of connected graphics vectors;

optically recognizing a subset of said binary array of picture components corresponding to said sets of connected character vectors and generating character identification codes corresponding to said picture components;

constructing an array of atoms and associated bond structure from said optimized sets of connected graphics vectors;

automatically interpreting chemical substructures character stings of characters to generate identified chemical substructures connection tables; and combining said chemical substructure connection tables with said array of atoms to generate a complete molecular structure file of atoms and associated bond structure.

13. The method of claim 12 wherein the step of generating character identification codes includes providing a set of template files representing known chemical structures and comparing said character identification codes with said template files to determine whether the character identification codes represent a known chemical substructure.

14. The method of claim 12 wherein the step of automatically interpreting chemical substructure character strings includes a chemical string processing method that applies rules of chemistry to convert the character identification codes into a recognized chemical substructures.

15. The method of claim 14 wherein the step of automatically interpreting chemical substructure character strings includes parsing a string of character identification codes and producing as output a molecular structure file representing a known chemical substructure.

16. The method of claim 15 wherein the step of automatically interpreting chemical substructure character strings includes parsing a string of character identification codes using a series of routines which isolate molecular group information from the string characters representing atoms and which divide the remaining string components into one or more defined substrings for separation into individual connectivity tables.

17. The method of claim 16 wherein said digital computer includes first and second state machines and first and second stacks, and the chemical string processing method includes separating molecular front information using said first state machine and said first stack for storing the molecular front information, and wherein the processing of character substrings is performed using said second state machine and said second stack.

18. The method of claim 14 wherein the step of automatically interpreting chemical substructure character strings includes separating molecular group information from string characters representing, a string treatment step for dividing an input character string into defined substrings for separate processing, parsing the characters of a substring and placing non-hydrogen atoms on a stack, determining the connectivity and coordinate positions between atoms on the stack and creating a molecular file for a character substring using the group information.

19. The method of claim 18 wherein the step of automatically interpreting chemical substructure character strings further includes testing the connectivity between atoms of the molecular structure file and modifying the molecular structure file to ensure that each atom is properly connected and that a valid chemical substructure has been created.

20. The method of claim 18 wherein said chemical substructure combining step includes the step of inserting the coordinate positions for said treated substrings to said molecular structure file.

21. An automated system for the optical recognition of chemical graphics comprising:
a digital processing apparatus including a central processing unit (CPU), an optical scanner for generating a two-dimensional binary array representation of a textual input, and a data storage medium for retaining and storing a series of instructions executable by the digital processing apparatus;
means for scanning an input of printed text having a chemical structure printed thereon, and generating a two-dimensional binary array representation of said text;
means for generating an isolated array subset of said binary array representation corresponding to said chemical structure;
means for generating a vector representation of said chemical structure from said isolated array subset;
means for segmenting said vector representation into sets of connected character vectors and sets of connected graphics vectors;
means for eliminating redundant vectors and vector junctions and generating optimized sets of connected graphics vectors from sa d sets of connected graphics vectors;
means for generating character identification codes corresponding to said connected character vector sets;
means for constructing an array of atoms and associated bond structure from said optimized sets of connected graphics vectors;
means for processing said character identification codes to produce an output of identified chemical substructures connection table; and
means for combining said chemical substructure connection tables with said array of atoms to generate a complete molecular file of atoms and associated bond structure.

22. The software system of claim 21 wherein said digital processing apparatus includes a state machine and a stack, and said executable instruction means includes means for controlling said state machine and stack to process said character identification codes to produce an output of identified chemical substructures.

* * * * *

UNITED STATES PATENT AND TRADEMARK OFFICE
CERTIFICATE OF CORRECTION

PATENT NO. : 5,157,736

DATED : October 20, 1992

INVENTOR(S) : Boyer et al.

It is certified that error appears in the above-identified patent and that said Letters Patent is hereby corrected as shown below:

Column 163, Claim 1, line 9: Change "ana" to --an--.

Column 165, Claim 1, line 8: Change "substrates" to --substructures--.

Column 165, Claim 7, line 45: Change "pints" to --points--.

Column 166, Claim 12, line 31: Change "substructures" to --substructure--.

Column 166, Claim 12, line 32: Change "stings" to --strings--.

Column 166, Claim 12, line 33: Change "substructures" to --substructure--.

Column 166, Claim 14, lines 49 and 50: Change "substructures" to --substructure--.

Column 168, Claim 21, line 24: Change "substructures" to --substructure--.

Signed and Sealed this

Twenty-eighth Day of September, 1993

Attest:

BRUCE LEHMAN

*Attesting Officer*  *Commissioner of Patents and Trademarks*